US008901372B2

(12) United States Patent
Hu et al.

(10) Patent No.: US 8,901,372 B2
(45) Date of Patent: Dec. 2, 2014

(54) PLANT RESISTANCE TO BANANA BUNCHY TOP VIRUS

(75) Inventors: John Hu, Honolulu, HI (US); Wayne Borth, Honolulu, HI (US); Eden A. Perez, Honolulu, HI (US); Kheng Cheah, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 213 days.

(21) Appl. No.: 12/712,893

(22) Filed: Feb. 25, 2010

(65) Prior Publication Data

US 2010/0218279 A1 Aug. 26, 2010

Related U.S. Application Data

(60) Provisional application No. 61/276,681, filed on Sep. 14, 2009, provisional application No. 61/208,667, filed on Feb. 25, 2009.

(51) Int. Cl.

| | |
|---|---|
| ***C12N 15/113*** | (2010.01) |
| ***C12N 15/34*** | (2006.01) |
| ***C12N 15/82*** | (2006.01) |
| ***A01H 5/00*** | (2006.01) |

(52) U.S. Cl.

CPC .................................. *C12N 15/8283* (2013.01)

USPC ........... 800/279; 435/468; 435/418; 435/419; 435/469; 435/470; 800/293; 800/294; 800/295; 800/285

(58) Field of Classification Search

USPC .......................................................... 800/285

See application file for complete search history.

(56) References Cited

U.S. PATENT DOCUMENTS

| | | | | |
|---|---|---|---|---|
| 6,127,604 | A | 10/2000 | Dale et al. | |
| 6,800,793 | B2 * | 10/2004 | Hanley-Bowdoin et al. | 800/279 |
| 2004/0068764 | A1 * | 4/2004 | Chu et al. | 800/279 |
| 2004/0121430 | A1 | 6/2004 | Dale et al. | |
| 2007/0016980 | A1 | 1/2007 | Lyznik et al. | |

FOREIGN PATENT DOCUMENTS

| | | |
|---|---|---|
| WO | 00/43494 | 7/2000 |

OTHER PUBLICATIONS

Zheng et al. (J. South China Agricultural Univ. (2005) 25:18-21.*

Waterhouse et al. Virus resistance and gene silencing in plants can be induced by simultaneous expression of sense and antisense RNA (1998) Proc. Nat. Acad. Sci. 95: 13959-13964.*

Lehner et al. How to use RNA interference (2004) Breif. Func. Genom. Prot. 3: 68-83.*

Ratcliff et al. A similarity between viral defense and gene silencing in plants (1997) Science 276: 1558-1560.*

GenBank Accession No. AF485783.1.*

Zheng et al. (2005) J. South China Agricultural Univ. 25:18-21.*

Waterhouse et al. (Proc. Nat. Acad. Sci. (1998) 95: 13959-13964.*

Thomas J.E., Banana Bunchy Top Virus. Encyclopedia of Virology, 5 vols. (B.W.J. Mahy and M.H.V. Van regenmortel, Editors), pp. 272-279 Oxford: Elsevier.*

Chellappan et al. (2004) Plant Mol. Biol. 56: 601-611.*

Praveen et al. (2006) Plant Cell Tiss. and Organ Cult. 84: 49-55.*

Tsao, T.T-H. et al. thesis for the degree of Doctor of Philosophy (2008) Centre for Tropical Crops and Biocommodities, Queensland University of Technology, Australia, pp. i-xii, 135-166.*

Valencia et al. (2004) Int. Congress on Musa, Penang, Malaysia, p. 34.*

Roy et al. (2006) Nucl. Acids Res. 34: 6362-6377.*

Becker, D. K. et al., "Genetic transformation of Cavendish banana (Musa spp. AAA group) cv 'Grand Nain' via microprojectile bombardment" Plant Cell Reports (2000) 19:229-234.

Dale, J. et al. "Strategies for the generation of virus resistant bananas" H. Atkinson, J. Dale, R. Harding, A. Kiggundu, K. Kunert, J. M. Muchwezi, L. Sagi, A. Viljoen (eds). (2003) Genetic transformation strategies to address the major constraints to banana and plaintain production in Africa. INIBAP: Montpellier (FRA), 130 p., pp. 108-118.

Thomas, J. E. "Banana Bunchy Top Virus" Encyclopedia of Virology, Third Edition (2008), vol. 1, pp. 272-279.

Zheng, Y. et al. "Construction of Plant Expression Vector of Fusion Genes with Banana Bunchy Top Virus Replicase and Cucumber Mosaic Virus Coat Protein" Journal of South China Agricultural University, (2005) vol. 26, No. 3, pp. 2-11.

Burns et al., "The Genome Organization of Banana Bunchy Top Virus: Analysis of Six ssDNA Components." Journal of General Virology, 76:1471-1482 (1995).

Harding et al., "Nucleotide Sequence of One Component of the Banana Bunchy Top Virus Genome Contains a Putative Replicase Gene." Journal of General Virology, 74:323-328 (1993).

Ganapathi et al., "Agrobacterium-mediated Transformation of Embryogenic Cell Suspensions of the Banana Cultivar Rasthali (AAB)." Plant Cell Rep., 20:157-162 (2001).

Khalil et al., "Regeneration of Banana (Musa spp. AAB cv. Dwarf Brazilian) via Secondary Somatic Embryogenesis." Plant Cell Rep., 20:1128-1134 (2002).

Lucioli et al., "Tomato Yellow Leaf Curl Sardinia Virus Rep-Derived Resistance to Homologous and Heterologous Geminiviruses Occurs by Different Mechanisms and Is Overcome if Virus-Mediated Transgene Silencing Is Activated.", Journal of Virology, 77(12):6785-6798 (2003).

(Continued)

*Primary Examiner* — Russell Kallis

*Assistant Examiner* — Steven Bernacki

(74) *Attorney, Agent, or Firm* — Ronald I. Einstein; Shayne Y. Huff; Nixon Peabody LLP

(57) ABSTRACT

This invention relates to a nucleic acid construct. The construct includes a nucleic acid molecule configured to silence Banana bunchy top virus (BBTV), a 5' DNA promoter sequence, and a 3' terminator sequence. The nucleic acid molecule, the promoter, and the terminator are operatively coupled to permit transcription of the nucleic acid molecule. The present invention also relates to expression vectors, host cells, and transgenic plants containing the nucleic acid construct of the present invention. Also disclosed are methods of imparting BBTV resistance to plants.

14 Claims, 10 Drawing Sheets

(56) References Cited

OTHER PUBLICATIONS

May et al., "Generation of Transgenic Banana (Musa acuminata) Plants via Agrobacterium-Mediated Transformation." Bio/tech, 13:486-492 (1995).

Pooggin, M., "RNAi Targeting of DNA Virus in Plants." Nature Biotechnology, 21:131-132 (2003).

Sagi et al., "Genetic Transformation of Banana and Plantain (Musa spp.) via Particle Bombardment." Bio/tech, 13:481-485 (1995);.

Seemanpillai et al., "Transcriptional Silencing of Geminiviral Promoter-Driven Transgenes Following Homologous Virus Infection." Molecular Plant-Microbe Interactions, 16(5):429-438 (2003).

Senior, I.J., "Uses of Plant Gene Silencing." Biotechnology and Genetic Engineering Reviews, 15:79-119 (1998).

Vanitharani et al., "Short Interfering RNA-mediated Interference of Gene Expression and Viral DNA Accumulation in Cultured Plant Cells." PNAS, 100(16):9632-9636 (2003).

Waterhouse et al., "Exploring Plant Genomes by RNA-Induced Gene Silencing." Nature Review: Genetics, 4:29-38 (2003).

Wesley et al., "Construct Design for Efficient, Effective and High-Throughput Gene Silencing in Plants." Plant Journal, 27(6):581-590 (2001)'.

* cited by examiner atatgtcccg agttagtgcg ccacgtaagc gctggggctt attattaccc ccagcgctcg 60
ggacgggaca tttgcatcta taaatagacc tcccccctct ccatttcaag atcatcatcg 120
acgacagaAT GGCGCGATAT GTGGTATGCT GGATGTTCAC CATCAACAAT CCCACAACAC 180
TACCAGTGAT GAGGGATGAG ATCAAATACA TGGTATATCA AGTGGAGAGG GGACAGGAGG 240
GTACTCGGCA TGTGCAAGGA TACGTGGAGA TGAAGAGACG AAGTTCTCTG AAGCAGATGA 300
GAGGCTTCTT CCCAGGCGCA CACCTTGAGA AACGAAAGGG AAGCCAAGAA GAAGCGCGGT 360
CATACTGTAT GAAGGAAGAT ACAAGAATCG AAGGTCCCTT CGAGTTTGGT GCATTTAAAT 420
TGTCATGTAA TGATAATTTA TTTGATGTCA TACAGGATAT GCGTGAAACG CACAAAAGGC 480
CTTTGGAGTA TTTATATGAT TGTCCTAACA CCTTCGATAG AAGTAAGGAT ACATTATACA 540
GAGTACAAGC AGAGATGAAT AAAACGAAGG CGATGAATAG CTGGAGAACT TCTTTCAGTG 600
CTTGGACATC AGAGGTGGAG AATATCATGG CGCAGCCATG TCATCGGAGA ATAATTTGGG 660
TCTATGGCCC AAATGGAGGA GAAGGAAAGA CAACGTATGC TAAACATCTA ATGAAGACGG 720
GAAATGCGTT TTATTCTCCA GGAGGAAAAT CATTGGATAT ATGTAGACTG TATAATTATG 780
AGGATATTGT TATATTTGAT ATCCCTAGAT GCAAAGAGGA TTATTTAAAT TATGGTTTAT 840
TAGAGGAATT TAAGAATGGA ATAATTCAAA GCGGGAAATA TGAACCCGTT TTGAAGATAG 900
TAGAATATGT CGAAGTCATT GTAATGGCTA ACTTCCTTCC GAAGGAAGGA ATCTTTTCTG 960
AAGATCGAAT AAAGTTGGTT TCTTGCTGAa caagtaatga ctttacagcg cacgctccga 1020
caaaagcaca ctatgacaaa agtacgggta tctgattaga tatcctaacg atctagggcc 1080
gtaggcccgt gagcaatgaa cggcgagatc

FIGURE 4

SEQUENCE LISTING

```
<160> NUMBER OF SEQ ID NOS: 29

<210> SEQ ID NO 1
<211> LENGTH: 1110
<212> TYPE: DNA
<213> ORGANISM: Banana bunchy top virus

<400> SEQUENCE: 1

atatgtcccg agttagtgcg ccacgtaagc gctggggctt attattaccc ccagcgctcg     60

ggacgggaca tttgcatcta taaatagacc tcccccctct ccatttcaag atcatcatcg    120

acgacagaat ggcgcgatat gtggtatgct ggatgttcac catcaacaat cccacaacac    180

taccagtgat gagggatgag atcaaataca tggtatatca agtggagagg ggacaggagg    240

gtactcggca tgtgcaagga tacgtggaga tgaagagacg aagttctctg aagcagatga    300

gaggcttctt cccaggcgca caccttgaga aacgaaaggg aagccaagaa gaagcgcggt    360

catactgtat gaaggaagat acaagaatcg aaggtccctt cgagtttggt gcatttaaat    420

tgtcatgtaa tgataattta tttgatgtca tacaggatat gcgtgaaacg cacaaaaggc    480

ctttggagta tttatatgat tgtcctaaca ccttcgatag aagtaaggat acattataca    540

gagtacaagc agagatgaat aaaacgaagg cgatgaatag ctggagaact tctttcagtg    600

cttggacatc agaggtggag aatatcatgg cgcagccatg tcatcggaga ataatttggg    660

tctatggccc aaatggagga gaaggaaaga caacgtatgc taaacatcta atgaagacgg    720

gaaatgcgtt ttattctcca ggaggaaaat cattggatat atgtagactg tataattatg    780

aggatattgt tatatttgat atccctagat gcaaagagga ttatttaaat tatggtttat    840

tagaggaatt taagaatgga ataattcaaa gcgggaaata tgaacccgtt ttgaagatag    900

tagaatatgt cgaagtcatt gtaatggcta acttccttcc gaaggaagga atcttttctg    960

aagatcgaat aaagttggtt tcttgctgaa caagtaatga ctttacagcg cacgctccga   1020

caaaagcaca ctatgacaaa agtacgggta tctgattaga tatcctaacg atctagggcc   1080

gtaggcccgt gagcaatgaa cggcgagatc                                    1110


<210> SEQ ID NO 2
<211> LENGTH: 286
<212> TYPE: PRT
<213> ORGANISM: Banana bunchy top virus

<400> SEQUENCE: 2

Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45
```

-continued

```
Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Gly Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

<210> SEQ ID NO 3
<211> LENGTH: 1111
<212> TYPE: DNA
<213> ORGANISM: Banana bunchy top virus

<400> SEQUENCE: 3

```
agcgctgggg cttattatta cccccagcgc tcgggacggg acatttgcat ctataaatag      60

acctcccccc tctccattac aagatcatca tcgacgacag aatggcgcga tatgtggtat     120

gctggatgtt caccatcaac aatcccacaa cactaccagt gatgagggat gagataaaat     180

atatggtata tcaagtggag aggggacagg agggtactcg tcatgtgcaa ggttatgtcg     240

agatgaagag acgaagttct ctgaagcaga tgagaggctt cttcccaggc gcacaccttg     300

agaaacgaaa gggaagccaa gaagaagcgc ggtcatactg tatgaaggaa gatacaagaa     360

tcgaaggtcc cttcgagttt ggtgcattta aattgtcatg taatgataat ttatttgatg     420

tcatacagga tatgcgtgaa acgcacaaaa ggcctttgga gtatttatat gattgtccta     480

acaccttcga tagaagtaag gatacattat acagagtaca agcagagatg aataaaacga     540

aggcgatgaa tagctggaga acttctttca gtgcttggac atcagaggtg gagaatatca     600

tggcgcagcc atgtcatcgg agaataattt gggtctatgg cccaaatgga ggagaaggaa     660

agacaacgta tgcaaaacat ctaatgaaga cgagaaatgc gttttattct ccaggaggaa     720

aatctttgga tatatgtaga ctgtataatt acgaggatat tgtaatattt gatattccaa     780
```

-continued

```
gatgcaaaga ggattattta aattatgggt tattagagga atttaagaat ggaataattc    840

aaagcgggaa atatgaaccc gttttgaaga tagtagaata tgtcgaagtc attgtaatgg    900

ctaacttcct tccgaaggaa ggaatctttt ctgaagatcg aataaagttg gtttcttgct    960

gaacaagtaa tgactttaca gcgcacgctc cgacaaaagc acactatgac aaaagtacgg   1020

gtatctgatt gggttatctt aacgatctag ggccgtaggc ccgtgagcaa tgaacggcga   1080

gatcagatgt cccgagttag tgcgccacgt a                                  1111
```

```
<210> SEQ ID NO 4
<211> LENGTH: 286
<212> TYPE: PRT
<213> ORGANISM: Banana bunchy top virus

<400> SEQUENCE: 4

Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285


<210> SEQ ID NO 5
<211> LENGTH: 1111
<212> TYPE: DNA
<213> ORGANISM: Banana bunchy top virus
```

<400> SEQUENCE: 5

```
agatgtcccg agttagtgcg ccacgtaagc gctggggctt attattaccc ccagcgctcg     60

ggacgggaca tttgcatcta taaatagacc tccccccctct ccattacaag atcatcatcg    120

acgacagaat ggcgcgatat gtggtatgct ggatgttcac catcaacaat cccacaacac    180

taccagtgat gagggatgag ttcaaatata tggtatatca agtggagagg ggacaggagg    240

gtactcgtca tgtgcaaggg tatgtcgaga tgaagagacg aagttctctg aggcagatga    300

gagccttctt tcctggcgca caccttgaga aacgaaaggg aagccaagaa gaagcgcggt    360

catactgtat gaaggaagat acaagaatcg aaggtccctt cgagtttggt gcatttaaat    420

tgtcatgtaa tgataattta tttgatgtca tacaggatat gcgtgaaacg cacaaaaggc    480

ctctggagta tttatatgat tgtcctaaca ccttcgatag aagtaaggat acattataca    540

gagtacaagc agagatgaat aaaacgaagg cgatgaatag ctggagaacg tctttcagtg    600

cttggacatc agaagtggag aatatcatgg cgcagccatg tcatcggaga ataatttggg    660

tctatggccc aaatggagga gaaggaaaga caacgtatgc aaaacatcta atgaagacga    720

agaatgcgtt ttattctcca ggaggaaaat cattggatat atgtagactg tataattacg    780

aggatattgt tatatttgat attccaagat gcaaagagga ttatttaaat tatgggttat    840

tagaggaatt taagaatgga ataattcaaa gcgggaaata tgaacccgtt ttgaagatag    900

tagaatatgt cgaagtcatt gtaatggcta acttccttcc gaaggaagga atcttttctg    960

aagatcgaat aaagttggtt tcttgctgaa caagtaatga ctttacagcg cacgctccga   1020

caaaagtaca ctatgacaaa agtaggggta tctgattggg ttatcttaac gatctagggc   1080

cgtaggcccg tgagcaatga acggcgagat c                                  1111
```

<210> SEQ ID NO 6
<211> LENGTH: 286
<212> TYPE: PRT
<213> ORGANISM: Banana bunchy top virus

<400> SEQUENCE: 6

```
Met Ala Arg Tyr Val Val Cys Trp Met Phe Thr Ile Asn Asn Pro Thr
1               5                   10                  15

Thr Leu Pro Val Met Arg Asp Glu Phe Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Arg Gln Met Arg Ala Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160
```

-continued

```
Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Lys Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285


<210> SEQ ID NO 7
<211> LENGTH: 1110
<212> TYPE: DNA
<213> ORGANISM: Banana bunchy top virus

<400> SEQUENCE: 7

agcgctgggg cttattatta cccccagcgc tcgggacggg acatttgcat ctataaatag     60

acctcccccc tctccattac aagatcatca tcgacgacag aatggcgcga tatgtggtat    120

gctggatgtt caccatcaac aatcccacaa cactaccagt gatgagggat gagatcaaat    180

atatggtata tcaagtggag aggggacagg agggtactcg tcatgtgcaa ggatatgtcg    240

agatgaagag acgaagctct ctgaagcaga tgagagcctt ctttcctggc gcacaccttg    300

agaaacgaaa gggaagccaa gaagaagcgc ggtcatactg tatgaaggaa gatacaagaa    360

tcgaaggtcc cttcgagttt ggtgcattta aattgtcatg taatgataat ttatttgatg    420

tcatacagga tatgcgtgaa acgcacaaaa ggcctttgga gtatttatat gattgtccta    480

acaccttcga tagaagtaag gatacattat acagagtaca agccgagatg aataaaacga    540

aggcgatgaa tagctggaga acgtctttca gtgcttggac atcagaggtg gagaatatca    600

tggcgcagcc atgtcatcgg agaataattt gggtctatgg cccaaatgga ggagaaggaa    660

agacaacgta tgcaaaacat ctaatgaaga cgaggaatgc gttttattct ccaggaggaa    720

aatctttgga tatatgtaga ctgtataatt acgaggatat tgttatattt gatattccaa    780

gatgcaaaga ggattattta aattatgggt tattagagga attcaagaat ggaataattc    840

aaagcgggaa atatgaaccc gttttgaaga tagtagaata tgtcgaagtc attgtaatgg    900

ctaacttcct tccgaaggaa ggaatctttt ctgaagatcg aataaagttg gtttcttgct    960

gaacaagtaa tgactttaca gcgcacgctc cgacaaaagt acactatgac aaaagtacgg   1020

gtatctgatt aggtatccta acgatctagg gccgtaggcc cgtgagcaat gaacggcgag   1080

atcagatgtc ccgagttagt gcgccacgta                                    1110


<210> SEQ ID NO 8
<211> LENGTH: 286
<212> TYPE: PRT
<213> ORGANISM: Banana bunchy top virus

<400> SEQUENCE: 8

Met Ala Arg Tyr Val Val Cys Trp Met Phe Thr Ile Asn Asn Pro Thr
```

-continued

```
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Ala Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285


<210> SEQ ID NO 9
<211> LENGTH: 1104
<212> TYPE: DNA
<213> ORGANISM: Banana bunchy top virus

<400> SEQUENCE: 9

agcgctgggg cttattatta cccccagcgc tcgggacggg acatttgcat ctataaatag     60

acctcccccc tctccactac atgatcgtca tcgtcgacag aaatggcgcg atatgtggta    120

tgctggatgt tcaccatcaa caatcccgcc tcactaccag tgatgcggga tgagttcaaa    180

tacatggtat atcaagtgga gaggggacag gagggtactc gtcatgtgca aggatacgtg    240

gagatgaaga gacgaagttc tctgaagcag atgagaggct tcttcccagg cgcacacctt    300

gagaaacgaa aggggagcca agaagaagca cgggcatact gtatgaagga agctacaaga    360

atcgaaggtc ccttcgagtt tggtgcattc aaattatcat gtaatgataa tttatttgat    420

gtcatacagg atatgcgtga aacgcataaa cggcctttgg aatatttata tgagtgtcct    480

aataccttcg atagaagtaa ggatacatta tacagagttc aagcggagtt gaataaaacg    540
```

-continued

```
aaggcgatga atagctggaa gacaaccttc agtacatgga cgtcggaagt tgaaaatata    600

atggcggagc catgtcatcg aaggataatt tgggtctacg gcccaaatgg aggcgaagga    660

aagacaactt atgcaaaaca tttaatgaag acgaagaatg cgttttattc tccaggagga    720

aaatcattgg atatatgtag attgtataat tatgaagaaa tagttatatt tgatattccc    780

agatgcaaag aggaatattt aaactacggt ttattagaag aattcaaaaa tggaattatt    840

caaagcggga aatatgaacc cgttttgaaa attgtagagt atgtggaagt cattgtcatg    900

gctaacttcc ttccgaagga aggaatcttt tctgaagatc gaataaagtt agttgcttgc    960

tgaacacgct atgccaatcg tacgctatga caaaaaggga aaagtaaaga atcgggggtt   1020

gattggtcta tcctaccgac aaagggccgc aggcccgtca agatggacgg cgagatcaga   1080

tgtcccgagt tagtgcgcca cgta                                          1104
```

```
<210> SEQ ID NO 10
<211> LENGTH: 286
<212> TYPE: PRT
<213> ORGANISM: Banana bunchy top virus

<400> SEQUENCE: 10

Met Ala Arg Tyr Val Val Cys Trp Met Phe Thr Ile Asn Asn Pro Ala
1               5                   10                  15

Ser Leu Pro Val Met Arg Asp Glu Phe Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ala Tyr Cys
65                  70                  75                  80

Met Lys Glu Ala Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Glu Cys Pro Asn Thr
        115                 120                 125

Phe Asp Arg Ser Lys Asp Thr Leu Tyr Arg Val Gln Ala Glu Leu Asn
    130                 135                 140

Lys Thr Lys Ala Met Asn Ser Trp Lys Thr Thr Phe Ser Thr Trp Thr
145                 150                 155                 160

Ser Glu Val Glu Asn Ile Met Ala Glu Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Lys Asn Ala Phe Tyr Ser Pro Gly Gly Lys Ser
        195                 200                 205

Leu Asp Ile Cys Arg Leu Tyr Asn Tyr Glu Glu Ile Val Ile Phe Asp
    210                 215                 220

Ile Pro Arg Cys Lys Glu Glu Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270
```

-continued

```
Glu Gly Ile Phe Ser Glu Asp Arg Ile Lys Leu Val Ala Cys
        275                 280                 285


<210> SEQ ID NO 11
<211> LENGTH: 1110
<212> TYPE: DNA
<213> ORGANISM: Banana bunchy top virus

<400> SEQUENCE: 11

atgtcccgag ttagtgcgcc acgtaagcgc tggggcttat tattaccccc agcgctcggg      60

acgggacatt tgcatctata aatagacctc ccccctctcc attacaagat catcatcgac     120

gacagaatgg cgcgatatgt ggtatgctgg atgttcacca tcaacaatcc cacaacacta     180

ccagtgatga gggatgagat caaatacatg gtatatcaag tggagagggg acaggagggt     240

actcgtcatg tgcaaggtta tgtcgagatg aagagacgaa gctctctgaa gcagatgaga     300

ggcttcttcc caggcgcaca ccttgagaaa cgaaagggaa gccaagaaga agcgcgatca     360

tactgtatga aggaagatac aagaatcgaa ggtcccttcg agtttggtgc atttaaattg     420

tcatgtaatg ataatttatt tgatgtcata caggatatgc gtgaaacgca caaaaggcct     480

ttggagtatt tatatgattg tcctaacacc gtcgatagaa gtaaggatac attatacaga     540

gtacaagcag agatgaataa aacgaaggcg atgaatagct ggagatcttc tttcagtgct     600

tggacatcag aggtggagaa tataatggcg cagccatgtc atcggagaat aatttgggtc     660

tatggcccaa atggaggaga aggaaagaca acgtatgcaa aacatctaat gaagacgaga     720

aatgcgtttt attctccagg aggaaaatca ttggatatat gtagactgta taattacgag     780

gatattgtta tacttgatat ccctagatgc aaagaggatt atttaaatta tggtttatta     840

gaggaattta agaatggaat aattcaaagc gggaaatatg aacccgtttt gaagattgta     900

gaatatgtcg aagtcattgt aatggctaac ttccttccga aggaaggaat cttctctgaa     960

gatcgaataa agttggtttc ttgctgaaca cgcaatgact ttacagcgca cgctccgaca    1020

aaagcacact atgacaaaag tatgggtatc tgattggtta tcctaacgat ctagggccgt    1080

aggcccgtga gcaatgaacg gcgagatcag                                     1110


<210> SEQ ID NO 12
<211> LENGTH: 286
<212> TYPE: PRT
<213> ORGANISM: Banana bunchy top virus

<400> SEQUENCE: 12

Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
```

-continued

```
        115                 120                 125

Val Asp Arg Ser Lys Asp Thr Leu Tyr Arg Val Gln Ala Glu Met Asn
    130                 135                 140

Lys Thr Lys Ala Met Asn Ser Trp Arg Ser Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Leu Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285


<210> SEQ ID NO 13
<211> LENGTH: 1111
<212> TYPE: DNA
<213> ORGANISM: Banana bunchy top virus

<400> SEQUENCE: 13

agatgtcccg agttagtgcg ccacgtaagc gctggggctt attattaccc ccagcgctcg     60

ggacgggaca tttgcatcta taactagacc tcccccctct ccattacaag atcatcatcg    120

acgacagaat ggcgcgatat gtggtatgct ggatgttcac catcaacaat cccacaacac    180

taccagtgat gagggatgag atcaaatata tggtatatca aatggagagg ggacaggagg    240

gtactcgtca tgtgcaaggt tatgtcgaga tgaagagacg aagctctctg aagcagatga    300

gaggcttctt cccaggcgca caccttgaga aacgaaaggg aacccaagaa gaagcgcggt    360

catactgtat gaaggaagat acaagaatcg aaggtccctt cgagtttggt acatttaaat    420

tgtcatgtaa tgacaattta tttgatgtca tacaggatat gcgtgaaacg cacaaaaggc    480

ctttggagta tttatatgat tgtcctaaca ccttcgatag aagtaaggat acattataca    540

gagtacaagc cgagatgaat aaacgaaggg cgatgaatag ctggaaaact tctttcagtg    600

catggacatc agaggtggag aatatcatgg cgcagccatg tcatcggaga ataatttggg    660

tctatggccc aaatggagga gaaggaaaga caacgtatgc aaaacatcta atgaagacga    720

gaaatgcgtt ttattctcca ggaggaaaat cattggatat atgtagactg tataattacg    780

aggatattgt tatatttgat attccaagat gcaaagagga ttatttaaat tatgggttat    840

tagaggaatt taagaatgga ataattcaaa gcgggaaata tgaacccgtt ttgaagatag    900

tagaatatgt cgaagtcatt gtaatggcta acttccttcc gaaggaagga atcttttctg    960

aagatcgaat aaagttggtt tcttgctgaa caagtaatga ctttacagcg cacgctccga   1020

caaaagcaca ctatgacaaa agtacgggta tctgattggt ttatcttaac gatctagggc   1080

cgtaggcccg tgagcaatga acggcgagat c                                  1111
```

-continued

<210> SEQ ID NO 14
<211> LENGTH: 286
<212> TYPE: PRT
<213> ORGANISM: Banana bunchy top virus

<400> SEQUENCE: 14

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Met
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Thr Gln Glu Glu Ala Arg Ser Tyr Cys
65                  70                  75                  80

Met Lys Glu Asp Thr Arg Ile Glu Gly Pro Phe Glu Phe Gly Thr Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Arg Arg Ala Met Asn Ser Trp Lys Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

<210> SEQ ID NO 15
<211> LENGTH: 1111
<212> TYPE: DNA
<213> ORGANISM: Banana bunchy top virus

<400> SEQUENCE: 15

```
agatgtcccg agttagtgcg ccacgtaagc gctggggctt attattaccc ccagcgctcg     60

ggacgggaca tttgcatcta taaatagacc tcccccctct ccattacaag atcatcatcg    120

acgacagaat ggcgcgatat gtggtatgct ggatgttcac catcaacaat cccacaacac    180

taccagtgat gagggatgag ataaaatata tggtatatca agtggagagg ggacaggagg    240

gtactcgtca tgtgcaaggt tatgtcgaga tgaagagacg aagctctctg aagcagatga    300
```

-continued

```
gaggcttctt cccaggcgca caccttgaga aacgaaaggg aagccaagaa gaagcgcggt    360

catactgtat gaaggaagat acaagaatcg aaggtccctt cgagtttggt tcatttaaat    420

tgtcatgtaa tgataattta tttgatgtca tacaggatat gcgtgaaacg cacaaaaggc    480

ctttggagta tttatatgat tgtcctaaca ccttcgatag aagtaaggat acattataca    540

gagtacaagc agagatgaat aaaacgaagg cgatgaatag ctggagaact tctttcagtg    600

cttggacatc agaggtggag aatatcatgg cgcagccatg tcatcggaga ataatttggg    660

tctatggccc aaatggagga gaaggaaaga caacgtatgc aaaacatcta atgaagacga    720

gaaatgcgtt ttattctcca ggaggaaaat cattggatat atgtagactg tataattacg    780

aggatattgt tatatttgat attccaagat gcaaagagga ttatttaaat tatgggttat    840

tagaggaatt taagaatgga ataattcaaa gcgggaaata tgaacccgtt ttgaagatag    900

tagaatatgt cgaagtcatt gtaatggcta acttccttcc gaaggaagga atcttttctg    960

aagatcgaat aaagttggtt tcttgctgaa caagtaatga ctttacagcg cacgctccga   1020

caaaagcaca ctatgacaaa agtacgggta tctgattggg ttatcttaac gatctagggc   1080

cgtaggcccg tgagcaatga acggcgagat c                                  1111
```

<210> SEQ ID NO 16
<211> LENGTH: 286
<212> TYPE: PRT
<213> ORGANISM: Banana bunchy top virus

<400> SEQUENCE: 16

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ser Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
```

```
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285


<210> SEQ ID NO 17
<211> LENGTH: 456
<212> TYPE: DNA
<213> ORGANISM: Banana bunchy top virus

<400> SEQUENCE: 17

gtaagcgctg gggcttatta ttacccccag cgctcgggac gggacatttg catctataaa     60

tagacctccc ccctctccat tacaagatca tcatcgacga cagaatggcg cgatatgtgg    120

tatgctggat gttcaccatc aacaatccca caacactacc agtgatgagg gatgagataa    180

aatatatggt atatcaagtg gagaggggac aggagggtac tcgtcatgtg caaggttatg    240

tcgagatgaa gagacgaagc tctctgaagc agatgagagg cttcttccca ggcgcacacc    300

ttgagaaacg aaagggaagc caagaagaag cgcggtcata ctgtatgaag gaagatacaa    360

gaatcgaagg tcccttcgag tttggttcat ttaaattgtc atgtaatgat aatttatttg    420

atgtcataca ggatatgcgt gaaacgcaca aaaggc                              456


<210> SEQ ID NO 18
<211> LENGTH: 31
<212> TYPE: DNA
<213> ORGANISM: Banana bunchy top virus

<400> SEQUENCE: 18

agcgctgggg cttattatta cccccagcgc t                                    31


<210> SEQ ID NO 19
<211> LENGTH: 17
<212> TYPE: DNA
<213> ORGANISM: Artificial
<220> FEATURE:
<223> OTHER INFORMATION: PCR Primer to amplify Banana bunchy top virus
      Rep gene

<400> SEQUENCE: 19

ccatcaacaa tcccaca                                                    17


<210> SEQ ID NO 20
<211> LENGTH: 20
<212> TYPE: DNA
<213> ORGANISM: Artificial
<220> FEATURE:
<223> OTHER INFORMATION: PCR Primer to amplify Banana bunchy top virus
      Rep gene

<400> SEQUENCE: 20

acagtatgac cgcgcttctt                                                 20


<210> SEQ ID NO 21
<211> LENGTH: 5
<212> TYPE: PRT
<213> ORGANISM: Banana bunchy top virus

<400> SEQUENCE: 21
```

```
Phe Thr Ile Asn Asn
1               5


<210> SEQ ID NO 22
<211> LENGTH: 5
<212> TYPE: PRT
<213> ORGANISM: Banana bunchy top virus

<400> SEQUENCE: 22

His Leu Gln Gly Tyr
1               5


<210> SEQ ID NO 23
<211> LENGTH: 5
<212> TYPE: PRT
<213> ORGANISM: Banana bunchy top virus

<400> SEQUENCE: 23

Tyr Cys Met Lys Glu
1               5


<210> SEQ ID NO 24
<211> LENGTH: 5
<212> TYPE: PRT
<213> ORGANISM: Banana bunchy top virus

<400> SEQUENCE: 24

Gly Glu Gly Lys Thr
1               5


<210> SEQ ID NO 25
<211> LENGTH: 40
<212> TYPE: PRT
<213> ORGANISM: Banana bunchy top virus

<400> SEQUENCE: 25

Val Val Cys Trp Met Phe Thr Ile Asn Asn Pro Thr Thr Leu Pro Val
1               5                   10                  15

Met Arg Asp Glu Ile Lys Tyr Met Val Tyr Gln Val Glu Arg Gly Gln
            20                  25                  30

Glu Gly Thr Arg His Val Gln Gly
        35                  40


<210> SEQ ID NO 26
<211> LENGTH: 39
<212> TYPE: PRT
<213> ORGANISM: Banana bunchy top virus

<400> SEQUENCE: 26

Tyr Val Glu Met Lys Arg Arg Ser Ser Leu Lys Gln Met Arg Gly Phe
1               5                   10                  15

Phe Pro Gly Ala His Leu Glu Lys Arg Lys Gly Ser Gln Glu Glu Ala
            20                  25                  30

Arg Ser Tyr Cys Met Lys Glu
        35


<210> SEQ ID NO 27
<211> LENGTH: 47
<212> TYPE: PRT
<213> ORGANISM: Banana bunchy top virus

<400> SEQUENCE: 27

Met Ala Gln Pro Cys His Arg Arg Ile Ile Trp Val Tyr Gly Pro Asn
```

-continued

```
1               5                   10                  15

Gly Gly Glu Gly Lys Thr Thr Tyr Ala Lys His Leu Met Lys Thr Gly
            20                  25                  30

Asn Ala Phe Tyr Ser Pro Gly Gly Lys Ser Leu Asp Ile Cys Arg
        35                  40                  45


<210> SEQ ID NO 28
<211> LENGTH: 43
<212> TYPE: PRT
<213> ORGANISM: Banana bunchy top virus

<400> SEQUENCE: 28

Leu Tyr Asn Tyr Glu Asp Ile Val Ile Phe Asp Ile Pro Arg Cys Lys
1               5                   10                  15

Glu Asp Tyr Leu Asn Tyr Gly Leu Leu Glu Glu Phe Lys Asn Gly Ile
            20                  25                  30

Ile Gln Ser Gly Lys Tyr Glu Pro Val Leu Lys
        35                  40


<210> SEQ ID NO 29
<211> LENGTH: 19
<212> TYPE: PRT
<213> ORGANISM: Banana bunchy top virus

<400> SEQUENCE: 29

Ile Val Glu Tyr Val Glu Val Ile Val Met Ala Asn Phe Leu Pro Lys
1               5                   10                  15

Glu Gly Ile
```

PLANT RESISTANCE TO BANANA BUNCHY TOP VIRUS

This application claims the priority benefit of U.S. Provisional Patent Application Ser. No. 61/208,667, filed Feb. 25, 2009, and U.S. Provisional Patent Application Ser. No. 61/276,681, filed Sep. 14, 2009, which are hereby incorporated by reference in their entirety.

This invention was made with government support under USDA-ARS Government Contract No. 58-5320-4-534. The government has certain rights in the invention.

FIELD OF THE INVENTION

The present invention relates to nucleic acid constructs configured to silence Banana bunchy top virus ("BBTV"), expression vectors, host cells, transgenic plants, and methods of imparting BBTV resistance.

BACKGROUND OF THE INVENTION

Banana bunchy top disease, caused by Banana bunchy top virus (BBTV), is the most serious viral disease of banana worldwide. BBTV is the type-member of the Babuvirus genus in the family Nanoviridae and is a single-stranded (+) sense DNA virus with at least six genomic components that are each packaged in separate virions (Burns et al., "The Genome Organization of Banana Bunchy Top Virus: Analysis of Six ssDNA Components," *Journal of General Virology* 76:1471-1482 (1995)). BBTV is transmitted within plantations by the banana aphid, *Pentalonia nigronervosa*, and is also transmitted through infected planting material (Magee, "Investigation on the Bunchy Top Disease of the Banana," *Council for Scientific and Industrial Research*, Bulletin 30 (1927)). Infected plants become chlorotic and stunted. More importantly, plants infected prior to the initiation of flowering will not form fruits. Additionally, the virus spreads systemically to all plants in the mat resulting in nonproductive areas within plantations. Virus incidence may reach 100%, resulting in total yield loss and abandonment of fields.

BBTV was first detected in the State of Hawaii on the island of Oahu in 1989 (Ferreira, "The Status of Moko and Bunchy Top Diseases in Hawaii," Research Ext. Service, CTAHR, UH Coop. Ext. Serv., Honolulu, Hi. (1991); Dietzgen et al., "Properties of Virus-like Particles Associated with Banana Bunchy Top Disease in Hawaii, Indonesia and Tonga," *Australasia Plant Pathology* 20:161-165 (1991)) and has since spread to the Kona area on Hawaii (1995), to Kauai (1997), to Maui (2002), and to the Hilo area on Hawaii (2003). Currently, BBTV is the limiting factor for banana production on the island of Oahu, and has the potential to destroy the banana industry in Hawaii.

Once BBTV is present in a plantation, it is very difficult to control. Control of the aphid vector using insecticides is expensive, has low efficiency, and poses environmental and health risks. Removal of infected mats is required to limit spread of the virus but requires identification of early symptoms as well as increased labor and chemical costs. Reliable, economical, and environmentally sound control strategies are needed for the efficient control of BBTV in Hawaii. Development of resistant varieties is an environmentally sound, economical, and effective way to control plant diseases. However, BBTV resistance has not been found in any *Musa* germplasm. Even with resistance available in the germplasm, traditional breeding for disease resistance in banana is exceptionally difficult since all cultivated varieties are sterile, seedless clones that are vegetatively propagated.

Advances in biotechnology have led to the successful development and commercial release of several virus resistant crops including papaya, squash, and tomato. Transformation of banana has been reported by Sagi et al., "Genetic Transformation of Banana and Plantain (*Musa* spp.) via Particle Bombardment,"*Bio/tech* 13:481-485 (1995); May et al., "Generation of Transgenic Banana (*Musa acuminata*) Plants via *Agrobacterium*-Mediated Transformation," Bio/tech 13:486-492 (1995); Becker et al., "Genetic Transformation of Cavendish Banana (*Musa* spp. AAA group) cv 'Grand Nain' via Microprojectile Bombardment," *Plant Cell Rep.* 19:229-234 (2000); and Ganaphthi et al., "*Agrobacterium*-mediated Transformation of Embryogenic Cell Suspensions of the Banana Cultivar Rasthali (AAB)," *Plant Cell Rep.* 20:157-162 (2001)).

Researchers have used both biolistic- and *Agrobacterium*-mediated methods to transform either meristematic regions or embryogenic tissues of banana. The major obstacle to the production of transgenic banana has been the regeneration of large numbers of wholly-transformed plants. One procedure involves using secondary embryogenesis that allows for the production and regeneration of large numbers of plants initiated from single cells which should be wholly transformed (Khalil et al., "Regeneration of Banana (*Musa* spp. AAB cv. Dwarf Brazilian) via Secondary Somatic Embryogenesis," *Plant Cell Rep.* 20:1128-1134 (2002)).

The present invention is directed to overcoming these and other limitations in the art.

SUMMARY OF THE INVENTION

One aspect of the present invention relates to a nucleic acid construct. The nucleic acid construct contains a nucleic acid molecule configured to silence Banana bunchy top virus (BBTV), a 5' DNA promoter, and a 3' terminator sequence. The nucleic acid molecule, the promoter, and the terminator are operatively coupled to permit transcription of the nucleic acid molecule.

The present invention also relates to expression vectors and host cells comprising the nucleic acid construct of the present invention.

Another aspect of the present invention relates to a transgenic plant transformed with the nucleic acid construct of the present invention.

The present invention also relates to component parts of the transgenic plant, or a fruit of the transgenic plant.

A further aspect of the present invention relates to a method of imparting BBTV resistance to a plant. This method involves transforming a plant or plant cell with a nucleic acid construct according to the present invention and growing the transformed plant or plant cell under conditions effective to impart BBTV resistance to the plant.

According to one embodiment, the present invention relates to nucleic acid constructs containing modified BBTV genes. Constructs containing full and/or partial BBTV genes have been introduced into the banana cultivar 'Dwarf Brazilian' and have successfully produced a number of banana plants that have increased resistance to BBTV as demonstrated by virus challenge with viruliferous aphids. The resistant plants contain genes from the transformation vectors, and these transgenes are not present in susceptible wild-type plants. The genetically engineered plants of the present invention represent the only banana of any variety that have demonstrable BBTV resistance. Since banana plants are exclusively vegetatively propagated, these resistant plants can be used to produce many individuals with the same resistance characteristics. Farmers who grow these resistant plants will be able to replant their fields in the usual way by transplanting young suckers that arise from recently-harvested resistant plants. These suckers will also have BBTV resistance. The approach developed is applicable to other banana varieties, with other useful horticultural characteristics.

BRIEF DESCRIPTION OF THE DRAWINGS

FIG. 1A illustrates genome component 1 of BBTV. TATA, putative tata box; SL-CR, stem-loop conserved region; MCR, major conserved region; Poly-A, poly-A tail. FIG. 1B illustrates binary transformation vector pBI121 engineered to contain four different BBTV Rep constructs (M1, AS1, PR1, and R/PR1) by replacement of the GUS coding region. (M1): Complete Rep gene with two single-point mutations. (✫) in M1 represents the two single point mutations. (AS1): Complete Rep in antisense orientation. (PR1): partial Rep gene in antisense orientation. (R/PR1): complete Rep gene fused to PR1 in antisense orientation.

FIG. 4 is an illustration of SEQ ID NO:1 of the present invention with markings to show features of the sequence. The underlined portion of the sequence is the stem loop of SEQ ID NO:18. The nucleotides in capital letters represent the Rep coding region. The nucleotides in bold type represent the partial Rep construct of SEQ ID NO:17. The nucleotides with double underscore represent the TATA box. The nucleotides with a dotted underscore represent the poly-A tail. The boxed-in nucleotides constitute the site of a AA→CT double-point mutation.

DETAILED DESCRIPTION OF THE INVENTION

Figure 1A:
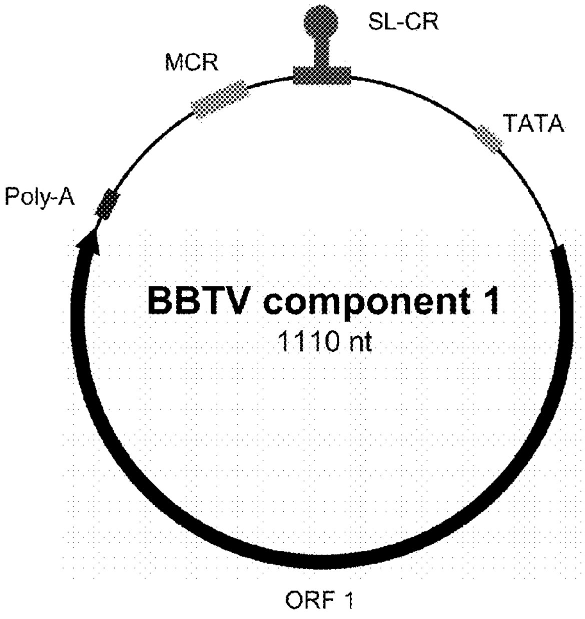
FIGS. 1A-B are schematic illustrations showing constructs used to transform banana embryogenic cell suspensions.

One aspect of the present invention relates to a nucleic acid construct. The nucleic acid construct contains a nucleic acid molecule configured to silence Banana bunchy top virus (BBTV), a 5' DNA promoter, and a 3' terminator sequence. The nucleic acid molecule, the promoter, and the terminator are operatively coupled to permit transcription of the nucleic acid molecule.

BBTV is a single-stranded (+) sense DNA virus with at least six genomic components that are each packaged in separate virions (Burns et al., "The Genome Organization of Banana Bunchy Top Virus: Analysis of Six ssDNA Components," *Journal of General Virology* 76:1471-1482 (1995), which is hereby incorporated by reference in its entirety).

An exemplary nucleic acid molecule suitable for the nucleic acid construct of the present invention includes, without limitation, the BBTV replication associated protein (Rep) gene. The Hawaiian isolate of the complete replication associated protein (Rep) gene (GenBank Accession No. U18077, which is hereby incorporated by reference in its entirety) has the nucleotide sequence of SEQ ID NO:1, as follows:

```
atatgtcccg agttagtgcg ccacgtaagc gctggggctt attattaccc ccagcgctcg    60
ggacgggaca tttgcatcta taaatagacc tcccccctct ccatttcaag atcatcatcg   120
acgacagaat ggcgcgatat gtggtatgct ggatgttcac catcaacaat cccacaacac   180
taccagtgat gagggatgag atcaaataca tggtatatca agtggagagg ggacaggagg   240
gtactcggca tgtgcaagga tacgtggaga tgaagagacg aagttctctg aagcagatga   300
gaggcttctt cccaggcgca caccttgaga aacgaaaggg aagccaagaa gaagcgcggt   360
catactgtat gaaggaagat acaagaatcg aaggtccctt cgagtttggt gcatttaaat   420
tgtcatgtaa tgataattta tttgatgtca tacaggatat gcgtgaaacg cacaaaaggc   480
ctttggagta tttatatgat tgtcctaaca ccttcgatag aagtaaggat acattataca   540
gagtacaagc agagatgaat aaaacgaagg cgatgaatag ctggagaact tctttcagtg   600
cttggacatc agaggtggag aatatcatgg cgcagccatg tcatcggaga ataatttggg   660
tctatggccc aaatggagga gaaggaaaga caacgtatgc taaacatcta atgaagacgg   720
gaaatgcgtt ttattctcca ggaggaaaat cattggatat atgtagactg tataattatg   780
```

-continued

```
aggatattgt tatatttgat atccctagat gcaaagagga ttatttaaat tatggtttat   840

tagaggaatt taagaatgga ataattcaaa gcgggaaata tgaacccgtt ttgaagatag   900

tagaatatgt cgaagtcatt gtaatggcta acttccttcc gaaggaagga atcttttctg   960

aagatcgaat aaagttggtt tcttgctgaa caagtaatga ctttacagcg cacgctccga  1020

caaaagcaca ctatgacaaa agtacgggta tctgattaga tatcctaacg atctagggcc  1080

gtaggcccgt gagcaatgaa cggcgagatc                                   1110
```

The coding region of SEQ ID NO:1 includes nucleotides 129-989. Other features of SEQ ID NO:1 are illustrated in FIG. 4 and described supra.

The protein encoded by the gene having the nucleotide sequence of SEQ ID NO:1 has an amino acid sequence of SEQ ID NO:2, as follows:

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Gly Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

Another isolate of the replication associated protein (Rep) gene suitable for the nucleic acid construct of the present invention is the sequence of GenBank Accession No. AB252640, which is hereby incorporated by reference in its entirety. This isolate has the nucleotide sequence of SEQ ID NO:3, as follows:

```
agcgctgggg cttattatta cccccagcgc tcgggacggg acatttgcat ctataaatag    60
acctcccccc tctccattac aagatcatca tcgacgacag aatggcgcga tatgtggtat   120
gctggatgtt caccatcaac aatcccacaa cactaccagt gatgagggat gagataaaat   180
atatggtata tcaagtggag aggggacagg agggtactcg tcatgtgcaa ggttatgtcg   240
agatgaagag acgaagttct ctgaagcaga tgagaggctt cttcccaggc gcacaccttg   300
agaaacgaaa gggaagccaa gaagaagcgc ggtcatactg tatgaaggaa gatacaagaa   360
tcgaaggtcc cttcgagttt ggtgcattta aattgtcatg taatgataat ttatttgatg   420
tcatacagga tatgcgtgaa acgcacaaaa ggcctttgga gtatttatat gattgtccta   480
acaccttcga tagaagtaag gatacattat acagagtaca agcagagatg aataaaacga   540
aggcgatgaa tagctggaga acttctttca gtgcttggac atcagaggtg gagaatatca   600
tggcgcagcc atgtcatcgg agaataattt gggtctatgg cccaaatgga ggagaaggaa   660
agacaacgta tgcaaaacat ctaatgaaga cgagaaatgc gttttattct ccaggaggaa   720
aatctttgga tatatgtaga ctgtataatt acgaggatat tgtaatattt gatattccaa   780
gatgcaaaga ggattattta aattatgggt tattagagga atttaagaat ggaataattc   840
aaagcgggaa atatgaaccc gttttgaaga tagtagaata tgtcgaagtc attgtaatgg   900
ctaacttcct tccgaaggaa ggaatctttt ctgaagatcg aataaagttg gtttcttgct   960
gaacaagtaa tgactttaca gcgcacgctc cgacaaaagc acactatgac aaaagtacgg  1020
gtatctgatt gggttatctt aacgatctag ggccgtaggc ccgtgagcaa tgaacggcga  1080
gatcagatgt cccgagttag tgcgccacgt a                                 1111
```

The coding region of SEQ ID NO:3 includes nucleotides 102-962.

The protein encoded by the gene having the nucleotide sequence of SEQ ID NO:3 has an amino acid sequence of SEQ ID NO:4, as follows:

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175
```

-continued

```
Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

Another isolate of the replication associated protein (Rep) gene suitable for the nucleic acid constructs of the present invention is the sequence of GenBank Accession No. AF102780, which is hereby incorporated by reference in its entirety. This isolate has the nucleotide sequence of SEQ ID NO:5, as follows:

```
agatgtcccg agttagtgcg ccacgtaagc gctggggctt attattaccc ccagcgctcg    60

ggacgggaca tttgcatcta taaatagacc tccccccctct ccattacaag atcatcatcg   120

acgacagaat ggcgcgatat gtggtatgct ggatgttcac catcaacaat cccacaacac   180

taccagtgat gagggatgag ttcaaatata tggtatatca agtggagagg ggacaggagg   240

gtactcgtca tgtgcaaggg tatgtcgaga tgaagagacg aagttctctg aggcagatga   300

gagccttctt tcctggcgca caccttgaga aacgaaaggg aagccaagaa gaagcgcggt   360

catactgtat gaaggaagat acaagaatcg aaggtccctt cgagtttggt gcatttaaat   420

tgtcatgtaa tgataattta tttgatgtca tacaggatat gcgtgaaacg cacaaaaggc   480

ctctggagta tttatatgat tgtcctaaca ccttcgatag aagtaaggat acattataca   540

gagtacaagc agagatgaat aaaacgaagg cgatgaatag ctggagaacg tctttcagtg   600

cttggacatc agaagtggag aatatcatgg cgcagccatg tcatcggaga ataatttggg   660

tctatggccc aaatggagga gaaggaaaga caacgtatgc aaaacatcta atgaagacga   720

agaatgcgtt ttattctcca ggaggaaaat cattggatat atgtagactg tataattacg   780

aggatattgt tatatttgat attccaagat gcaaagagga ttatttaaat tatgggttat   840

tagaggaatt taagaatgga ataattcaaa gcgggaaata tgaacccgtt ttgaagatag   900

tagaatatgt cgaagtcatt gtaatggcta acttccttcc gaaggaagga atcttttctg   960

aagatcgaat aaagttggtt tcttgctgaa caagtaatga ctttacagcg cacgctccga  1020

caaaagtaca ctatgacaaa agtaggggta tctgattggg ttatcttaac gatctagggc  1080

cgtaggcccg tgagcaatga acggcgagat c                                 1111
```

The coding region of SEQ ID NO:5 includes nucleotides 129-989.

The protein encoded by the gene having the nucleotide sequence of SEQ ID NO:5 has an amino acid sequence of SEQ ID NO:6, as follows:

```
Met Ala Arg Tyr Val Val Cys Trp Met Phe Thr Ile Asn Asn Pro Thr
1               5                   10                  15

Thr Leu Pro Val Met Arg Asp Glu Phe Lys Tyr Met Val Tyr Gln Val
            20                  25                  30
```

-continued

```
Glu Arg Gly Gln Glu Gly Thr Arg His Val Gln Gly Tyr Val Glu Met
        35                  40                  45

Lys Arg Arg Ser Ser Leu Arg Gln Met Arg Ala Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Lys Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

Another isolate of the replication associated protein (Rep) gene suitable for the nucleic acid constructs of the present invention is the sequence of GenBank Accession No. AM418535, which is hereby incorporated by reference in its entirety. This isolate has the nucleotide sequence of SEQ ID NO:7, as follows:

```
agcgctgggg cttattatta cccccagcgc tcgggacggg acatttgcat ctataaatag    60

acctcccccc tctccattac aagatcatca tcgacgacag aatggcgcga tatgtggtat   120

gctggatgtt caccatcaac aatcccacaa cactaccagt gatgagggat gagatcaaat   180

atatggtata tcaagtggag aggggacagg agggtactcg tcatgtgcaa ggatatgtcg   240

agatgaagag acgaagctct ctgaagcaga tgagagcctt ctttcctggc gcacaccttg   300

agaaacgaaa gggaagccaa gaagaagcgc ggtcatactg tatgaaggaa gatacaagaa   360

tcgaaggtcc cttcgagttt ggtgcattta aattgtcatg taatgataat ttatttgatg   420

tcatacagga tatgcgtgaa acgcacaaaa ggcctttgga gtatttatat gattgtccta   480

acaccttcga tagaagtaag gatacattat acagagtaca agccgagatg aataaaacga   540

aggcgatgaa tagctggaga acgtctttca gtgcttggac atcagaggtg gagaatatca   600

tggcgcagcc atgtcatcgg agaataattt gggtctatgg cccaaatgga ggagaaggaa   660

agacaacgta tgcaaaacat ctaatgaaga cgaggaatgc gttttattct ccaggaggaa   720

aatctttgga tatatgtaga ctgtataatt acgaggatat tgttatattt gatattccaa   780
```

-continued

```
gatgcaaaga ggattattta aattatgggt tattagagga attcaagaat ggaataattc   840

aaagcgggaa atatgaaccc gttttgaaga tagtagaata tgtcgaagtc attgtaatgg   900

ctaacttcct tccgaaggaa ggaatctttt ctgaagatcg aataaagttg gtttcttgct   960

gaacaagtaa tgactttaca gcgcacgctc cgacaaaagt acactatgac aaaagtacgg  1020

gtatctgatt aggtatccta acgatctagg gccgtaggcc cgtgagcaat gaacggcgag  1080

atcagatgtc ccgagttagt gcgccacgta                                   1110
```

The coding region of SEQ ID NO:7 includes nucleotides 102-962.

The protein encoded by the gene having the nucleotide sequence of SEQ ID NO:7 has an amino acid sequence of SEQ ID NO:8, as follows:

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Ala Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

Another isolate of the replication associated protein (Rep) gene suitable for the nucleic acid constructs of the present invention is the sequence of GenBank Accession No. AY450396, which is hereby incorporated by reference in its entirety. This isolate has the nucleotide sequence of SEQ ID NO:9, as follows:

```
agcgctgggg cttattatta cccccagcgc tcgggacggg acatttgcat ctataaatag    60
acctcccccc tctccactac atgatcgtca tcgtcgacag aaatggcgcg atatgtggta   120
tgctggatgt tcaccatcaa caatcccgcc tcactaccag tgatgcggga tgagttcaaa   180
tacatggtat atcaagtgga gaggggacag gagggtactc gtcatgtgca aggatacgtg   240
gagatgaaga gacgaagttc tctgaagcag atgagaggct tcttcccagg cgcacacctt   300
gagaaacgaa aggggagcca agaagaagca cgggcatact gtatgaagga agctacaaga   360
atcgaaggtc ccttcgagtt tggtgcattc aaattatcat gtaatgataa tttatttgat   420
gtcatacagg atatgcgtga aacgcataaa cggcctttgg aatatttata tgagtgtcct   480
aataccttcg atagaagtaa ggatacatta tacagagttc aagcggagtt gaataaaacg   540
aaggcgatga atagctggaa gacaaccttc agtacatgga cgtcggaagt tgaaaatata   600
atggcggagc catgtcatcg aaggataatt tgggtctacg gcccaaatgg aggcgaagga   660
aagacaactt atgcaaaaca tttaatgaag acgaagaatg cgttttattc tccaggagga   720
aaatcattgg atatatgtag attgtataat tatgaagaaa tagttatatt tgatattccc   780
agatgcaaag aggaatattt aaactacggt ttattagaag aattcaaaaa tggaattatt   840
caaagcggga aatatgaacc cgttttgaaa attgtagagt atgtggaagt cattgtcatg   900
gctaacttcc ttccgaagga aggaatcttt tctgaagatc gaataaagtt agttgcttgc   960
tgaacacgct atgccaatcg tacgctatga caaaaaggga aaagtaaaga atcgggggtt  1020
gattggtcta tcctaccgac aaagggccgc aggcccgtca agatggacgg cgagatcaga  1080
tgtcccgagt tagtgcgcca cgta                                         1110
```

The coding region of SEQ ID NO:9 includes nucleotides 103-963.

The protein encoded by the gene having the nucleotide sequence of SEQ ID NO:9 has an amino acid sequence of SEQ ID NO:10, as follows:

```
Met Ala Arg Tyr Val Val Cys Trp Met Phe Thr Ile Asn Asn Pro Ala
1               5                   10                  15

Ser Leu Pro Val Met Arg Asp Glu Phe Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ala Tyr Cys
65                  70                  75                  80

Met Lys Glu Ala Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Glu Cys Pro Asn Thr
        115                 120                 125

Phe Asp Arg Ser Lys Asp Thr Leu Tyr Arg Val Gln Ala Glu Leu Asn
    130                 135                 140

Lys Thr Lys Ala Met Asn Ser Trp Lys Thr Thr Phe Ser Thr Trp Thr
145                 150                 155                 160

Ser Glu Val Glu Asn Ile Met Ala Glu Pro Cys His Arg Arg Ile Ile
                165                 170                 175
```

-continued

```
Trp Val Tyr Gly Pro Asn Gly Gly Glu Gly Lys Thr Thr Tyr Ala Lys
            180                 185                 190

His Leu Met Lys Thr Lys Asn Ala Phe Tyr Ser Pro Gly Gly Lys Ser
        195                 200                 205

Leu Asp Ile Cys Arg Leu Tyr Asn Tyr Glu Glu Ile Val Ile Phe Asp
    210                 215                 220

Ile Pro Arg Cys Lys Glu Glu Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ala Cys
        275                 280                 285
```

Another isolate of the replication associated protein (Rep) gene suitable for the nucleic acid constructs of the present invention is the sequence of GenBank Accession No. EF095162, which is hereby incorporated by reference in its entirety. This isolate has the nucleotide sequence of SEQ ID NO:11, as follows:

```
atgtcccgag ttagtgcgcc acgtaagcgc tggggcttat tattaccccc agcgctcggg    60
acgggacatt tgcatctata aatagacctc ccccctctcc attacaagat catcatcgac   120
gacagaatgg cgcgatatgt ggtatgctgg atgttcacca tcaacaatcc cacaacacta   180
ccagtgatga gggatgagat caaatacatg gtatatcaag tggagagggg acaggagggt   240
actcgtcatg tgcaaggtta tgtcgagatg aagagacgaa gctctctgaa gcagatgaga   300
ggcttcttcc caggcgcaca ccttgagaaa cgaaagggaa gccaagaaga agcgcgatca   360
tactgtatga aggaagatac aagaatcgaa ggtcccttcg agtttggtgc atttaaattg   420
tcatgtaatg ataatttatt tgatgtcata caggatatgc gtgaaacgca caaaaggcct   480
ttggagtatt tatatgattg tcctaacacc gtcgatagaa gtaaggatac attatacaga   540
gtacaagcag agatgaataa aacgaaggcg atgaatagct ggagatcttc tttcagtgct   600
tggacatcag aggtggagaa tataatggcg cagccatgtc atcggagaat aatttgggtc   660
tatggcccaa atggaggaga aggaaagaca acgtatgcaa aacatctaat gaagacgaga   720
aatgcgtttt attctccagg aggaaaatca ttggatatat gtagactgta taattacgag   780
gatattgtta tacttgatat ccctagatgc aaagaggatt atttaaatta tggtttatta   840
gaggaattta agaatggaat aattcaaagc gggaaatatg aacccgtttt gaagattgta   900
gaatatgtcg aagtcattgt aatggctaac ttccttccga aggaaggaat cttctctgaa   960
gatcgaataa agttggtttc ttgctgaaca cgcaatgact ttacagcgca cgctccgaca  1020
aaagcacact atgacaaaag tatgggtatc tgattggtta tcctaacgat ctagggccgt  1080
aggcccgtga gcaatgaacg gcgagatcag                                   1110
```

The coding region of SEQ ID NO:11 includes nucleotides 127-987.

The protein encoded by the gene having the nucleotide sequence of SEQ ID NO:11 has an amino acid sequence of SEQ ID NO:12, as follows:

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30
```

-continued

```
Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ala Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Val Asp Arg Ser Lys Asp Thr Leu Tyr Arg Val Gln Ala Glu Met Asn
    130                 135                 140

Lys Thr Lys Ala Met Asn Ser Trp Arg Ser Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Leu Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

Another isolate of the replication associated protein (Rep) gene suitable for the nucleic acid constructs of the present invention is the sequence of GenBank Accession No. EU140342, which is hereby incorporated by reference in its entirety. This isolate has the nucleotide sequence of SEQ ID NO:13, as follows:

```
agatgtcccg agttagtgcg ccacgtaagc gctggggctt attattaccc ccagcgctcg    60

ggacgggaca tttgcatcta taactagacc tccccccctct ccattacaag atcatcatcg   120

acgacagaat ggcgcgatat gtggtatgct ggatgttcac catcaacaat cccacaacac   180

taccagtgat gagggatgag atcaaatata tggtatatca aatggagagg ggacaggagg   240

gtactcgtca tgtgcaaggt tatgtcgaga tgaagagacg aagctctctg aagcagatga   300

gaggcttctt cccaggcgca caccttgaga aacgaaaggg aacccaagaa gaagcgcggt   360

catactgtat gaaggaagat acaagaatcg aaggtccctt cgagtttggt acatttaaat   420

tgtcatgtaa tgacaattta tttgatgtca tacaggatat gcgtgaaacg cacaaaaggc   480

ctttggagta tttatatgat tgtcctaaca ccttcgatag aagtaaggat acattataca   540

gagtacaagc cgagatgaat aaacgaaggg cgatgaatag ctggaaaact tctttcagtg   600

catggacatc agaggtggag aatatcatgg cgcagccatg tcatcggaga ataatttggg   660

tctatggccc aaatggagga gaaggaaaga caacgtatgc aaaacatcta atgaagacga   720

gaaatgcgtt ttattctcca ggaggaaaat cattggatat atgtagactg tataattacg   780
```

-continued

```
aggatattgt tatatttgat attccaagat gcaaagagga ttatttaaat tatgggttat   840

tagaggaatt taagaatgga ataattcaaa gcgggaaata tgaacccgtt ttgaagatag   900

tagaatatgt cgaagtcatt gtaatggcta acttccttcc gaaggaagga atcttttctg   960

aagatcgaat aaagttggtt tcttgctgaa caagtaatga ctttacagcg cacgctccga  1020

caaaagcaca ctatgacaaa agtacgggta tctgattggt ttatcttaac gatctagggc  1080

cgtaggcccg tgagcaatga acggcgagat c                                 1111
```

The coding region of SEQ ID NO:13 includes nucleotides 129-989.

The protein encoded by the gene having the nucleotide sequence of SEQ ID NO:13 has an amino acid sequence of SEQ ID NO:14, as follows:

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Met
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Thr Gln Glu Glu Ala Arg Ser Tyr Cys
65                  70                  75                  80

Met Lys Glu Asp Thr Arg Ile Glu Gly Pro Phe Glu Phe Gly Thr Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Arg Arg Ala Met Asn Ser Trp Lys Thr Ser Phe Ser Ala Trp Thr
145                 150                 155                 160

Ser Glu Val Glu Asn Ile Met Ala Gln Pro Cys His Arg Arg Ile Ile
                165                 170                 175

Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

Another isolate of the replication associated protein (Rep) gene suitable for the nucleic acid constructs of the present invention is the sequence of GenBank Accession No. S56276, which is hereby incorporated by reference in its entirety. This isolate has the nucleotide sequence of SEQ ID NO:15, as follows:

```
agatgtcccg agttagtgcg ccacgtaagc gctggggctt attattaccc ccagcgctcg     60
ggacgggaca tttgcatcta taaatagacc tccccccctct ccattacaag atcatcatcg   120
acgacagaat ggcgcgatat gtggtatgct ggatgttcac catcaacaat cccacaacac    180
taccagtgat gagggatgag ataaaatata tggtatatca agtggagagg ggacaggagg    240
gtactcgtca tgtgcaaggt tatgtcgaga tgaagagacg aagctctctg aagcagatga    300
gaggcttctt cccaggcgca caccttgaga aacgaaaggg aagccaagaa gaagcgcggt    360
catactgtat gaaggaagat acaagaatcg aaggtccctt cgagtttggt tcatttaaat    420
tgtcatgtaa tgataattta tttgatgtca tacaggatat gcgtgaaacg cacaaaaggc    480
ctttggagta tttatatgat tgtcctaaca ccttcgatag aagtaaggat acattataca    540
gagtacaagc agagatgaat aaaacgaagg cgatgaatag ctggagaact tctttcagtg    600
cttggacatc agaggtggag aatatcatgg cgcagccatg tcatcggaga ataatttggg    660
tctatggccc aaatggagga gaaggaaaga caacgtatgc aaaacatcta atgaagacga    720
gaaatgcgtt ttattctcca ggaggaaaat cattggatat atgtagactg tataattacg    780
aggatattgt tatatttgat attccaagat gcaaagagga ttatttaaat tatgggttat    840
tagaggaatt taagaatgga ataattcaaa gcgggaaata tgaacccgtt ttgaagatag    900
tagaatatgt cgaagtcatt gtaatggcta acttccttcc gaaggaagga atcttttctg    960
aagatcgaat aaagttggtt tcttgctgaa caagtaatga ctttacagcg cacgctccga   1020
caaaagcaca ctatgacaaa agtacgggta tctgattggg ttatcttaac gatctagggc   1080
cgtaggcccg tgagcaatga acggcgagat c                                  1111
```

The coding region of SEQ ID NO:15 includes nucleotides 129-989.

The protein encoded by the gene having the nucleotide sequence of SEQ ID NO:15 has an amino acid sequence of SEQ ID NO:16, as follows:

```
Met Ala Arg Tyr Val Val Cys Trp Met Phe Thr Ile Asn Asn Pro Thr
1               5                   10                  15

Thr Leu Pro Val Met Arg Asp Glu Ile Lys Tyr Met Val Tyr Gln Val
            20                  25                  30

Glu Arg Gly Gln Glu Gly Thr Arg His Val Gln Gly Tyr Val Glu Met
        35                  40                  45

Lys Arg Arg Ser Ser Leu Lys Gln Met Arg Gly Phe Phe Pro Gly Ala
    50                  55                  60

His Leu Glu Lys Arg Lys Gly Ser Gln Glu Glu Ala Arg Ser Tyr Cys
65                  70                  75                  80

Met Lys Glu Asp Thr Arg Ile Glu Gly Pro Phe Glu Phe Gly Ser Phe
                85                  90                  95

Lys Leu Ser Cys Asn Asp Asn Leu Phe Asp Val Ile Gln Asp Met Arg
            100                 105                 110

Glu Thr His Lys Arg Pro Leu Glu Tyr Leu Tyr Asp Cys Pro Asn Thr
        115                 120                 125

Phe Asp Arg Ser Lys Asp Thr Leu Tyr Arg Val Gln Ala Glu Met Asn
    130                 135                 140

Lys Thr Lys Ala Met Asn Ser Trp Arg Thr Ser Phe Ser Ala Trp Thr
145                 150                 155                 160

Ser Glu Val Glu Asn Ile Met Ala Gln Pro Cys His Arg Arg Ile Ile
                165                 170                 175
```

-continued

```
Trp Val Tyr Gly Pro Asn Gly Gly Glu Gly Lys Thr Thr Tyr Ala Lys
            180                 185                 190

His Leu Met Lys Thr Arg Asn Ala Phe Tyr Ser Pro Gly Gly Lys Ser
        195                 200                 205

Leu Asp Ile Cys Arg Leu Tyr Asn Tyr Glu Asp Ile Val Ile Phe Asp
    210                 215                 220

Ile Pro Arg Cys Lys Glu Asp Tyr Leu Asn Tyr Gly Leu Leu Glu Glu
225                 230                 235                 240

Phe Lys Asn Gly Ile Ile Gln Ser Gly Lys Tyr Glu Pro Val Leu Lys
                245                 250                 255

Ile Val Glu Tyr Val Glu Val Ile Val Met Ala Asn Phe Leu Pro Lys
            260                 265                 270

Glu Gly Ile Phe Ser Glu Asp Arg Ile Lys Leu Val Ser Cys
        275                 280                 285
```

Other isolates of the replication associated protein (Rep) gene are known and are also suitable nucleic acid molecules of the nucleic acid constructs of the present invention.

In addition, nucleic acid molecules having a nucleotide sequence which is at least 90% similar, at least 91% similar, at least 92% similar, at least 93% similar, at least 94% similar, at least 95% similar, at least 96% similar, at least 97% similar, at least 98% similar, or at least 99% similar to the nucleotide sequences of SEQ ID NO:1, 3, 5, 7, 9, 11, 13, or 15 are also suitable nucleic acid molecules of the nucleic acid constructs of the present invention. Similarly, nucleic acid molecules that encode an amino acid molecule having an amino acid sequence which is at least 90% similar, at least 91% similar, at least 92% similar, at least 93% similar, at least 94% similar, at least 95% similar, at least 96% similar, at least 97% similar, at least 98% similar, or at least 99% similar to the amino acid sequence of SEQ ID NO: 2, 4, 6, 8, 10, 12, 14, or 16 are also suitable nucleic acid molecules of the nucleic acid constructs of the present invention.

The determination of percent identity (i.e., sequence similarity) between two amino acid sequences or two nucleotide sequences can be accomplished using a mathematical algorithm. A preferred, non-limiting example of a mathematical algorithm utilized for the comparison of two sequences is the algorithm of Karlin et al., "Methods for Assessing the Statistical Significance of Molecular Sequence Features by Using General Scoring Schemes," *Proc. Natl. Acad. Sci.* 87:2264-2268 (1990), which is hereby incorporated by reference in its entirety, modified as in Karlin et al., "Applications and Statistics for Multiple High-Scoring Segments in Molecular Sequences," *Proc. Natl. Acad. Sci.* 90:5873-5877 (1993), which is hereby incorporated by reference in its entirety. Another non-limiting example of a mathematical algorithm utilized for the comparison of sequences is the algorithm of Myers et al., CABIOS (1989). Such an algorithm can be incorporated into the ALIGN program (version 2.0) which is part of the CGC sequence alignment software package. Additional algorithms for sequence analysis are known in the art and include ADVANCE and ADAM as described in Torellis et al. "ADVANCE and ADAM: Two Algorithms for the Analysis of Global Similarity between Homologous Informational Sequences," *Comput. Appl. Biosci.* 10:3-5 (1994), which is hereby incorporated by reference in its entirety, and FASTA described in Pearson et al., "Improved Tools for Biological Sequence Comparison," *Proc. Natl. Acad. Sci.* 85:2444-8 (1988), which is hereby incorporated by reference in its entirety.

Other suitable nucleic acid molecules of the nucleic acid constructs of the present invention include, without limitation, partial BBTV replication associated protein (Rep) gene isolates. In one embodiment, particularly suitable partial BBTV replication associated protein (Rep) gene isolates are, or include, nucleotide sequences that encode a rolling circle replication ("RCR") domain, an ATPase domain, a Viral Replicase motif, an RNA Helicase motif, or any combination of these motifs/domains. See, e.g., Njoroge et al., "Towards Transgenic Resistance to Banana Bunchy Top Virus (BBTV) by Expression of Defective Viral Reps," *ISHS/ProMusa Banana Symposium*, Guangzhou, China (Sep. 14-18, 2009), which is hereby incorporated by reference in its entirety.

One motif in the RCR domain of Rep is FTINN (SEQ ID NO:21). Another motif in the RCR domain of Rep is HLQGY (SEQ ID NO:22). A further motif in the RCR domain of Rep is YCMKE (SEQ ID NO:23). Nucleic acid molecules that encode any one or more of these motifs, or an amino acid molecule with a minor variation (e.g., only 1 amino acid difference) of SEQ ID NO:21, SEQ ID NO:22, or SEQ ID NO:23, may also be suitable nucleic acid molecules for the nucleic acid constructs of the present invention. The variation in the amino acid sequence may or may not be accounted for by the geographic isolate variation of BBTV.

One motif in the ATPase domain of Rep is the ATPase domain GE GKT (SEQ ID NO:24). Nucleic acid molecules that encode this motif or a minor variant (e.g., 1 amino acid difference), may also be suitable nucleic acid molecules for the nucleic acid constructs of the present invention. See Harding et al., "Nucleotide Sequence of One Component of the Banana Bunchy Top Virus Genome Contains a Putative Replicase Gene," *Journal of General Virology* 74:323-328 (1993), which is hereby incorporated by reference in its entirety. The variation in the amino acid sequence may or may not be accounted for by the isolate variation of BBTV.

One Viral Replicase motif is the amino acid sequence of SEQ ID NO:25, as follows: VVCWMFTINN PTTLPVMRDE IKYMVYQVER GQEGTRHVQG. The amino acid sequence of SEQ ID NO:25 is a partial sequence (residues 5-44) of SEQ ID NO:2. Another Viral Replicase motif is the amino acid sequence of SEQ ID NO:26, as follows: YVEMKRRSSL KQMRGFFPGA HLEKRKGSQE EARSYCMKE. The amino acid sequence of SEQ ID NO:26 is a partial sequence (residues 45-83) of SEQ ID NO:2. Suitable nucleic acid molecules of the nucleic acid constructs of the present invention include nucleic acid molecules that encode one or both of the Viral Replicase motifs of SEQ ID NO:25 and SEQ ID NO:26. Similarly, nucleic acid molecules that encode an amino acid molecule having an amino acid sequence which is a minor variant (e.g., has only 1, 2, 3, or 4 amino acid differences) of SEQ ID NO:25 or SEQ ID NO:26, are also encompassed by the present invention. The variation in the amino acid sequence may or may not be accounted for by the isolate variation of BBTV.

One RNA Helicase motif is the amino acid sequence of SEQ ID NO:27, as follows: MAQPCHRRII WVYGP-NGGEG KTTYAKHLMK TGNAFYSPGG KSLDICR. The amino acid sequence of SEQ ID NO:27 is a partial sequence (residues 167-213) of SEQ ID NO:2. Another RNA Helicase motif is the amino acid sequence of SEQ ID NO:28, as follows: LYNYEDIVIF DIPRCKEDYL NYGLLEEFKN GIIQSGKYEP VLK. The amino acid sequence of SEQ ID NO:28 is a partial sequence (residues 214-256) of SEQ ID NO:2. A further RNA Helicase motif is the amino acid sequence of SEQ ID NO:29, as follows: IVEYVEVIVM ANFLPKEGI. The amino acid sequence of SEQ ID NO:29 is a partial sequence (residues 257-275) of SEQ ID NO:2. Suitable nucleic acid molecules of the nucleic acid constructs of the present invention include nucleic acid molecules that encode one, two, or all three of the Viral Replicase motifs of SEQ ID NO:27, SEQ ID NO:28, and SEQ ID NO:29. Similarly, nucleic acid molecules that encode an amino acid molecule having an amino acid sequence which is a minor variant (e.g., has only 1, 2, or 3 amino acid differences) of SEQ ID NO:27, SEQ ID NO:28, or SEQ ID NO:29, are also encompassed by the present invention. The variation in the amino acid sequence may or may not be accounted for by the isolate variation of BBTV.

Another suitable partial BBTV replication associated protein (Rep) gene is from the Hawaiian BBTV isolate and has a sequence of SEQ ID NO:17, as follows:

```
gtaagcgctg gggcttatta ttacccccag cgctcgggac gggacatttg catctataaa  60
tagacctccc ccctctccat tacaagatca tcatcgacga cagaatggcg cgatatgtgg 120
tatgctggat gttcaccatc aacaatccca caacactacc agtgatgagg gatgagataa 180
aatatatggt atatcaagtg gagaggggac aggagggtac tcgtcatgtg caaggttatg 240
tcgagatgaa gagacgaagc tctctgaagc agatgagagg cttcttccca ggcgcacacc 300
ttgagaaacg aaagggaagc caagaagaag cgcggtcata ctgtatgaag gaagatacaa 360
gaatcgaagg tcccttcgag tttggttcat ttaaattgtc atgtaatgat aatttatttg 420
atgtcataca ggatatgcgt gaaacgcaca aaaggc                           456
```

This partial nucleotide sequence of SEQ ID NO:1 includes the stem-loop motif (bases 4-34 of SEQ ID NO:17), the potential TATA-box motif (bases 55-60 of SEQ ID NO:17), and the first 352 bases (bases 105-456 of SEQ ID NO:17) of the coding region of the replication associated protein (Rep) gene from the Hawaiian isolate of BBTV (SEQ ID NO:1).

Other BBTV replication associated protein (Rep) partial gene fragments are also suitable for the nucleic acid constructs of the present invention. According to one embodiment, these partial Rep gene fragments have a nucleotide sequence which is at least 90% similar, at least 91% similar, at least 92% similar, at least 93% similar, at least 94% similar, at least 95% similar, at least 96% similar, at least 97% similar, at least 98% similar, or at least 99% similar to the nucleotide sequence of SEQ ID NO:17.

BBTV replication associated protein (Rep) gene fragments can be synthesized by using PCR techniques together with specific sets of primers chosen to represent particular portions of the Rep gene of interest. These then would be cloned into an appropriate vector for expression of a truncated peptide or protein.

Chemical synthesis can also be used to make suitable partial BBTV replication associated protein (Rep) gene. Such a synthesis is carried out using known amino acid sequences for the protein being produced. Alternatively, subjecting a full length BBTV replication associated protein to high temperatures and pressures will produce fragments. These fragments can then be separated by conventional procedures (e.g., chromatography, SDS-PAGE).

Variants of BBTV replication associated protein (Rep) gene may also (or alternatively) be made and used in nucleic acid constructs of the present invention, for example, by the deletion or addition of amino acids that have minimal influence on the properties, secondary structure, and hydropathic nature of the protein. For example, a protein may be conjugated to a signal (or leader) sequence at the N-terminal end of the protein which co-translationally or post-translationally directs transfer of the protein. The protein may also be conjugated to a linker or other sequence for ease of synthesis, purification, or identification of the protein.

Nucleic acid molecules suitable for the nucleic acid constructs of the present invention are configured in the nucleic acid construct in a manner that results in silencing of any BBTV. For example, the nucleic acid molecule may be configured to result in suppression or interference of BBTV.

According to one embodiment of the present invention, the nucleic acid construct results in interference of BBTV expression by sense or co-suppression in which the nucleic acid molecule of the construct is in a sense (5'→3') orientation. Co-suppression has been observed and reported in many plant species and may be subject to a transgene dosage effect or, in another model, an interaction of endogenous and transgene transcripts that results in aberrant mRNAs (Senior, "Uses of Plant Gene Silencing," *Biotechnology and Genetic Engineering Reviews* 15:79-119 (1998); Waterhouse et al., "Exploring Plant Genomes by RNA-Induced Gene Silencing," *Nature Review: Genetics* 4:29-38 (2003), which are hereby incorporated by reference in their entirety). A construct with the nucleic acid molecule in the sense orientation may also give sequence specificity to RNA silencing when inserted into a vector along with a construct of both sense and antisense nucleic acid orientations as described infra (Wesley et al., "Construct Design for Efficient, Effective and High-Throughput Gene Silencing in Plants," *Plant Journal* 27(6): 581-590 (2001), which is hereby incorporated by reference in its entirety).

In one embodiment, the nucleic acid construct of the present invention has a nucleic acid molecule that is a sense form of the BBTV replication associated protein (Rep) gene having a mutation that renders a protein encoded by the BBTV replication associated protein (Rep) gene non-functional. For example, the mutation may include a mutation in the ATPase domain of the BBTV replication associated protein (Rep) gene. By way of another example, the mutation is an AA to CT mutation at the location identified by the boxed-in nucleotides of FIG. 4 (SEQ ID NO:1). A corresponding double-point mutation may also be made in, e.g., SEQ ID NO:3, 4, 7, 9, 11, 13, or 15.

In another embodiment, the nucleic acid construct of the present invention results in interference of BBTV expression by the use of antisense suppression in which the nucleic acid molecule of the construct is an antisense (3'→5') orientation. The use of antisense RNA to down-regulate the expression of specific plant genes is well known (van der Krol et al., "An Antisense Chalcone Synthase Gene in Transgenic Plants Inhibits Flower Pigmentation," *Nature* 333:866-869 (1988) and Smith et al., "Antisense RNA Inhibition of Polygalacturonase Gene Expression in Transgenic Tomatoes," *Nature* 334:724-726 (1988), which are hereby incorporated by reference in their entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). In the target cell, the antisense nucleic acids hybridize to a target nucleic acid and interfere with transcription, and/or RNA processing, transport, translation, and/or stability. The overall effect of such interference with the target nucleic acid function is the disruption of protein expression (Baulcombe, "Mechanisms of Pathogen-Derived Resistance to Viruses in Transgenic Plants," *Plant Cell* 8:1833-44 (1996); Dougherty et al., "Transgenes and Gene Suppression Telling Us Something New?" *Current Opinion in Cell Biology* 7:399-405 (1995); Lomonossoff, "Pathogen-Derived Resistance to Plant Viruses," *Ann. Rev. Phytopathol.* 33:323-43 (1995), which are hereby incorporated by reference in their entirety). Accordingly, in one embodiment of the present invention, the nucleic acid construct contains a nucleic acid molecule inserted into the nucleic acid construct in antisense orientation.

In one embodiment, the nucleic acid construct of the present invention has a nucleic acid that is the antisense form of the BBTV replication associated protein (Rep) gene. In an alternative embodiment, the nucleic acid construct of the present invention is an antisense form of a partial BBTV replication associated protein (Rep) gene. The antisense form of a partial BBTV replication associated protein (Rep) gene may include a conserved stem loop structure proximate to an end of the partial BBTV replication associated protein (Rep) gene. A conserved stem loop structure may include the sequence of SEQ ID NO:18, as follows:

```
AGCGCTGGGGCTTATTATTACCCCCAGCGCT
```

Interference of BBTV expression may also be achieved by the generation of double-stranded RNA ("dsRNA") through the use of inverted-repeats, segments of gene-specific sequences oriented in both sense and antisense orientations. In one embodiment, sequences in the sense and antisense orientations are linked or fused and inserted into a suitable expression vector having the appropriate 5' and 3' regulatory nucleotide sequences operably linked for transcription. The expression vector having the modified nucleic acid molecule is then inserted into a suitable host cell or subject. A third segment may link the two segments of sense and antisense orientation. This third segment may be any nucleotide sequence, such as a fragment of the gene specific sequences. When inverted repeats of nucleic acid molecules are employed, the sense and antisense segments may be oriented either head-to-head or tail-to-tail in the construct.

Alternatively, constructs of the present invention may encode both sense and antisense orientation molecules having separate promoters and no third segment linking the sense and antisense sequences (Chuang et al., "Specific and Heritable Genetic Interference by Double-Stranded RNA in *Arabidopsis thaliana,*" *Proc. Nat'l Academy of Sciences USA* 97(9):4985-4990 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety).

Other types of constructs are known to silence gene expression. For example, hairpin RNA ("hpRNA") which may also be characterized as dsRNA, involves RNA hybridizing with itself to form a hairpin structure that comprises a single-stranded loop region and a base-paired stem. Though a linker may be used between the inverted repeat segments of sense and antisense sequences to generate hairpin or double-stranded RNA, the use of intron-free hpRNA can also be used to achieve silencing of e.g., BBTV expression.

According to one embodiment of the nucleic acid construct of the present invention, the nucleic acid molecule comprises a first segment which is a sense form of the BBTV replication associated protein (Rep) gene and a second segment which is an antisense form of a partial BBTV replication associated protein (Rep) gene, where the first and second segments are linked to one another. According to this embodiment, the conserved stem loop sequence of, e.g., SEQ ID NO:18 (or a functional equivalent thereof) is included in the nucleic acid molecule proximate to an end of the first segment. In another embodiment, the conserved stem loop sequence of, e.g., SEQ ID NO:18 (or a functional equivalent thereof) is included in the nucleic acid molecule proximate to an end of the second segment. The first segment may be positioned in the construct so as to be transcribed before the second segment.

The BBTV replication associated protein (Rep) gene nucleotide sequences may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBI121, pBI525, pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y., Cold Spring Harbor Press (1989), and Ausubel et al., *Current Protocols in Molecular Biology*, New York, N.Y., John Wiley & Sons (1989), which are hereby incorporated by reference in their entirety.

In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA ("T-DNA") is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). In the present invention, the parent vector used was pGPTV-KAN. Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase ("NOS") gene promoter, from *Agrobacterium tumefaciens* (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); and McNellis et al., "Glucocorticoid-Inducible Expression of a Bacterial Avirulence Gene in Transgenic *Arabidopsis* Induces Hypersensitive Cell Death," *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known by those of ordinary skill in the art (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters Used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the Chrysanthemum UEP1 Promoter and Comparative Expression in Florets and Leaves of *Dendranthema grandiflora*," *Transgenic Res.* 11:437-445 (2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimaeric Granule-Bound Starch Synthase-GUS Gene in Transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

The nucleic acid construct of the present invention includes an operable 3' regulatory region, selected from among those which are capable of providing correct transcription termination and polyadenylation of mRNA for expression in the host cell of choice, operably linked to a nucleic acid molecule configured to silence BBTV. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus $^{35}$S Promoter," *Nature* 313(6005):810-812 (1985), which is hereby incorporated by reference in its entirety). Virtually any 3' regulatory region known to be operable in plants would be suitable for use in conjunction with the present invention.

The different components described supra can be ligated together to produce the expression systems which contain the nucleic acid constructs of the present invention, using well known molecular cloning techniques as described in Sambrook et al., *Molecular Cloning: A Laboratory Manual*, Second Edition Cold Spring Harbor, N.Y., Cold Spring Harbor Press (1989), and Ausubel et al. *Current Protocols in Molecular Biology*, New York, N.Y., John Wiley & Sons (1989), which are hereby incorporated by reference in their entirety.

Once the nucleic acid construct of the present invention has been prepared, it is ready to be incorporated into a host cell. Accordingly, another aspect of the present invention relates to a recombinant host cell containing one or more of the nucleic acid constructs of the present invention. Basically, this method is carried out by transforming a host cell with a nucleic acid construct of the present invention under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct of the present invention. As described supra, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," *Proc. Natl. Acad. Sci. USA* 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, microinjection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures, Vol.* 1, New York, N.Y., MacMillan Publishing Co. (1983); Vasil, ed., *Cell Culture and Somatic Cell Genetics of Plants*, Vol. I (1984) and Vol. III (1986), Orlando, Acad. Press; and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y., Cold Spring Harbor Press (1989), which is hereby incorporated by reference in its entirety).

Component parts and fruit of plants transformed with the nucleic acid construct of the present invention are encompassed by the present invention.

The present invention can be utilized in conjunction with a wide variety of plants, including, plants of the genus *Musa*. Plants can include, for example and without limitation, plants that become infected by BBTV, such as banana and plantain.

Another aspect of the present invention relates to a method of imparting BBTV resistance to a plant. This method involves transforming a plant or plant cell with a nucleic acid construct according to the present invention and growing the transformed plant or plant cell under conditions effective to impart BBTV resistance to the plant.

EXAMPLES

The following examples are provided to illustrate embodiments of the present invention but are by no means intended to limit its scope.

Example 1

Gene Constructs

Figure 1B:
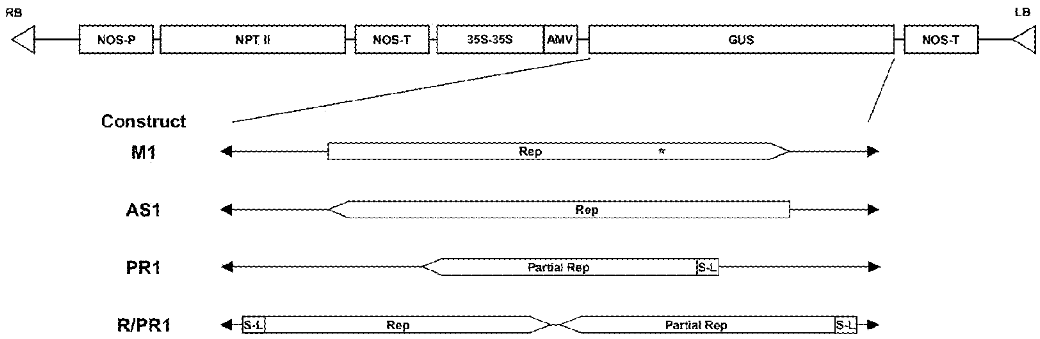
Figure 6:
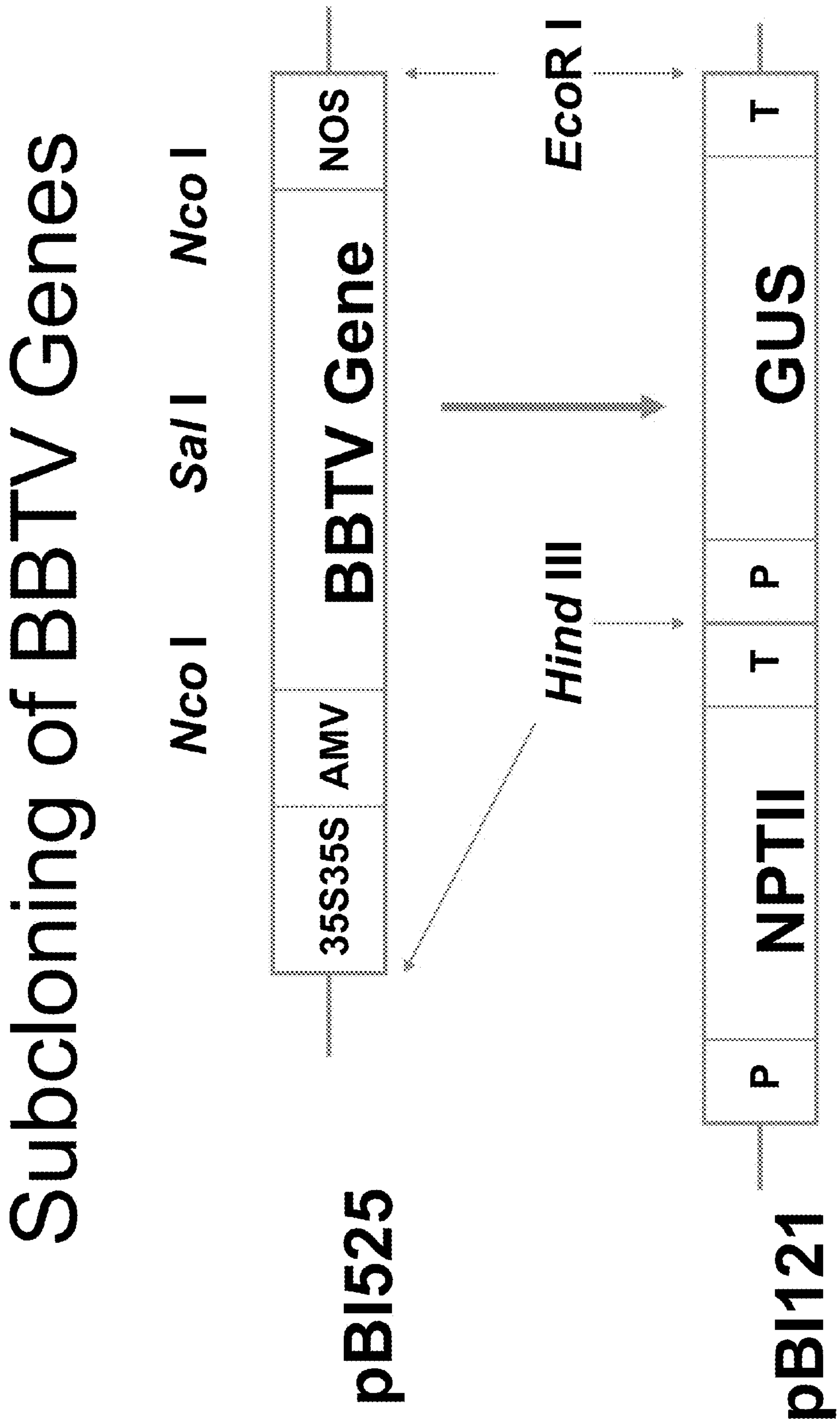
FIG. 6 is a schematic illustration showing the subcloning of BBTV genes into pBI121. (P): NOS promoter, (T): NOS terminator.

Four constructs were created from the BBTV replication associated protein (Rep) gene (FIG. 1B and FIG. 4). All constructs (M1, AS1, PR1, and R/PR1) were created in the transformation vector pBI121 by replacing the GUS gene in the native vector with one of the Rep constructs (FIG. 6).

Construct M1: Replication-associated protein (Rep) gene ORF from component 1 of the Hawaiian BBTV isolate, including the entire coding region of the replication-associated protein (Rep) gene containing two single-point mutations and the polyA-tail motif. Also included were 52 bp of the 5'-UTR including the putative TATA box, and 36 bp of the 3'-UTR both from component 1 of the Hawaiian BBTV isolate. All constructs were in sense orientation relative to the promoter, enhancer, and terminator in the vector.

Construct AS 1: Replication-associated protein (Rep) gene ORF from component 1 of the Hawaiian BBTV isolate, including the entire coding region of the replication-associated protein (Rep) gene and the polyA-tail motif. Also included were 52 bp of the 5'-UTR including the putative TATA box, and 36 bp of the 3'-UTR both from component 1 of the Hawaiian BBTV isolate. All constructs were in antisense orientation relative to the promoter, enhancer, and terminator in the vector.

Construct PR1: The first 352 bp from the 5'-end of the replication-associated protein (Rep) gene ORF from component 1 of the Hawaiian isolate of BBTV. Also included was 104 bp of the 5'-UTR immediately upstream from the replication-associated protein (Rep) gene ORF from component 1 of the Hawaiian BBTV isolate which contains the conserved stem-loop motif and the potential TATA box motif. All constructs were in antisense orientation relative to the promoter, enhancer, and terminator in the vector.

Construct R/PR1: The replication-associated protein (Rep) gene ORF from component 1 of the Hawaiian BBTV isolate that includes the entire coding region of the replication-associated protein (Rep) gene and the polyA-tail motif. Also included were 104 bp of the 5'-UTR including the putative TATA box, and the conserved stem-loop motif, both from component 1 of the Hawaiian BBTV isolate. This construct was in sense orientation relative to the promoter, enhancer, and terminator in the vector. Fused to the 3'-end of this entire construct, in antisense orientation, was the first 352 bp from the 5'-end of the replication-associated protein (Rep) gene ORF from component 1 of the Hawaiian isolate of BBTV and 104 bp of the 5'-UTR immediately upstream from the replication-associated protein (Rep) gene ORF which contains the conserved stem-loop motif and the potential TATA box motif from component 1 of the Hawaiian BBTV isolate. The resulting construct is composed of the entire ORF of the replication-associated protein (Rep) gene ORF including the 5'-UTR and 3'-UTR in sense orientation, fused to the first 352 bp from the 5'-end of the replication-associated protein (Rep) gene ORF and including 104 bp of the 5'-UTR immediately upstream from the replication-associated protein (Rep) gene ORF that contains the conserved stem-loop motif and the potential TATA box motif.

Example 2

Transformation and Regeneration of Transgenic Banana Lines

Embryogenic cell suspensions ("ECS") initiated from immature male flowers of 'Dwarf Brazilian' banana were established and transformed using *Agrobacterium tumefaciens* containing one of four constructs derived from the Rep gene of BBTV in binary vector pBI121 (FIGS. 1A-B). Transformed cell lines were selected on kanamycin, induced to form shoots and roots, and established in soil-less potting mix in the greenhouse.

Example 3

Polymerase Chain Reaction

DNA was isolated from lamina of the first fully expanded leaves of banana plants using the Plant DNeasy® Mini kit (Qiagen, Inc.) with modifications. All DNAs were quantified on a Nanoprop® spectrophometer and adjusted to 10 ng/μl with water. Primers designed to amplify a 209 bp fragment of the BBTV Rep gene were synthesized and used in polymerase chain reaction assays to detect the Rep gene in transgenic plants. The sequence of the forward primer: 5'-CCATCAACAATCCCACA-3' (SEQ ID NO:19) and the reverse primer: 5'-ACAGTATGACCGCGCTTCTT-3' (SEQ ID NO:20). All reaction volumes were 50 μA and contained: 1× TaqGold® reaction buffer, 1.5 mM $MgCl_2$, 200 μM each dNTP, 400 μM each primer, and 0.2 units TaqGold® polymerase. Cycling conditions were 95° C. for 10 minutes; followed by 35 cycles of 95° C. for 30 seconds, 50° C. for 30 seconds, 72° C. for 60 seconds; followed by 10 minutes at 72° C. 10 μL of each reaction was resolved on a 1.5% agarose gel in 1×TAE buffer, stained in ethidium bromide, and photographed under UV light.

Example 4

Inoculation of Putative Transgenic Lines with BBTV

Plants at the 4- to 6-leaf stage were challenged with BBTV-viruliferous aphids (*Pentalonia nigronervosa* Coq.) reared on BBTV-infected banana plants. Insects were allowed inoculation access times of 2-4 weeks, after which they were removed by insecticide application. All plants were observed for development of bunchy top symptoms for 6-12 months in the greenhouse.

Example 5

Southern Hybridization

Plants that showed no symptoms after challenge with BBTV were analyzed by Southern hybridization using a DIG-labelled probe to a portion of the NPT II gene. Total nucleic acids were isolated from leaf lamina using a modified CTAB procedure. Fresh leaf tissues (~200 mg) were collected, ground to a fine powder in liquid nitrogen, and added to 8 mL CTAB buffer (4% CTAB, 100 mM Tris-Cl, 20 mM EDTA, 1.4 M NaCl, 1% PVP, 0.1% 2-mercaptoethanol, pH=8.0) and incubated at 65° C. for 30 minutes with occasional mixing. This mixture was then emulsified with 8 mL chloroform:isoamyl alcohol (24:1) and 5 mL of the aqueous phase recovered by centrifugation. Nucleic acids were precipitated with 5 mL ice-cold isopropanol overnight at −20° C., recovered by centrifugation, washed two times with 70% ethanol, dried, and resuspended in 500 μL TE. Nucleic acids were quantified on a Nanoprop® spectrophotometer, and approximately 10 μg was digested overnight at 37° C. with 120 units EcoRI restriction endonuclease. No EcoRI sites were predicted to occur in any of the Rep gene constructs used to transform the banana. A single EcoR1 site is present in vector pBI121 located between the 3'-terminal NOS-terminator and the left border. Following digestion, nucleic acids were recovered by precipitation with ethanol and resuspended in 25 μL TE. The entire 25 μL of each sample was loaded into wells of a 0.7% agarose gel in 0.5×TBE and electrophoresced in 0.5×TBE at <1 V/cm for 16 hrs. Following electrophoresis, gels were stained in ethidium bromide and photographed under UV light to estimate loading of each sample. Gels were then denatured in 1.5 M NaCl:0.5 M NaOH, neutralized in 1.5 M NaCl:1.0 M Tris-Cl pH=7.4, and equilibrated in 10 SSC before nucleic acids were capillary-transferred to positively-charged nylon membranes (Roche, Inc.) in 10 SSC. After transfer, membranes were cross-linked with UV light (1200 μjoules).

Membranes were prehybridized in PerfectHyb Plus® solution (Sigma-Aldrich, Inc.) at 68° C. and hybridized at 68° C. overnight in PerfectHyb Plus® with a probe to the NPTII gene of pBI121 DIG-labelled by PCR according to the manufacturer's protocol. Following hybridization, membranes were washed twice in 2×SSC:0.1% SDS, and twice in 0.5× SSC:0.1% SDS before DIG-hybridization signals were detected according to the manufacturer's protocol (Roche, Inc.).

Example 6

Establishment of Transgenic Lines

Two hundred seventy banana lines, each transformed by *Agrobacterium* containing the plasmid pBI121 with one of four constructs of the Rep gene from the Hawaiian isolate of BBTV, were generated from embryogenic cell suspension cultures of the cultivar 'Dwarf Brazilian' (Table 1). All of these lines survived selection on media containing kanamycin. These plant lines were established in the greenhouse and challenged by *Pentalonia nigronervosa* that had been reared on BBTV-infected banana plants.

TABLE 1

Bunchy top symptoms on transgenic banana plant lines after inoculation with BBTV.

| Symptoms | M1 | AS1 | PR1 | R/PR1 | pBI121 |
|---|---|---|---|---|---|
| + | 31 | 69 | 33 | 116 | 63 |
| − | 1 | 5 | 5 | 10 | 0 |
| Total | 32 | 74 | 38 | 126 | 63 |

Plant lines M1, AS1, PR1, and R/PR1 are as in FIG. 1B. Line pBI121 is transformed with empty vector. (+) plants developed bunchy top symptoms. (−) plants remained symptom-free. (Total) total number of plants challenged with viruliferous aphids.

Example 7

Bunchy Top Symptoms in Transgenic Lines Challenged with BBTV

Of the 270 putatively transgenic banana plants that were established in pots in the greenhouse, a total of 21 lines did not develop symptoms 6-12 months after inoculation with BBTV. All of the control lines that were transformed with only the empty vector, and the majority of the transgenic plants, developed typical symptoms during this time.

Example 8

PCR Analyses

Figure 2A:
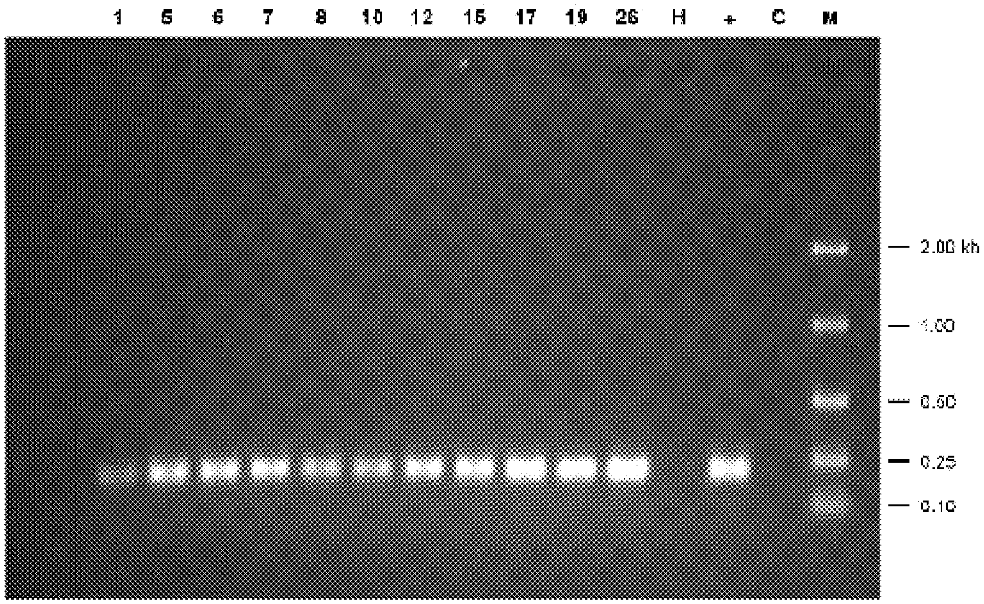
FIGS. 2A-B show the presence of the Rep transgene in putatively transformed banana detected by polymerase chain reaction ("PCR"). Lane numbers correspond to transgenic lines. (H): DNA from healthy banana plant. (+): DNA from BBTV-infected banana plant. (C): Water only control. (M): Molecular weight markers. Approximately 20 ng DNA sample was used in each PCR.
Figure 2B:
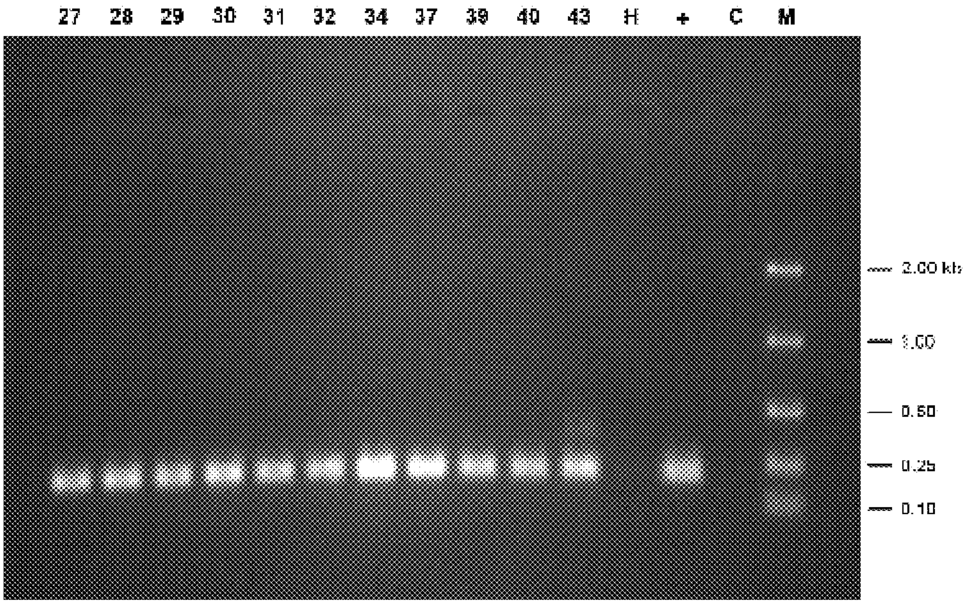

DNA extracted from all of the 21 transgenic lines that were resistant to BBTV, and banana plants infected with BBTV produced amplicons of the expected size in PCR. No amplification products were produced from DNA extracted from healthy banana plants, or control reactions that contained no DNA (FIGS. 2A-B). DNA isolated from the BBTV-resistant banana plants did not produce any amplicons in PCR analyses with primers designed to amplify BBTV coat protein gene sequences, confirming that these lines were not simply tolerant of BBTV infection, but that no BBTV was detectable in these plant lines.

Example 9

Southern Analyses

Figure 3:
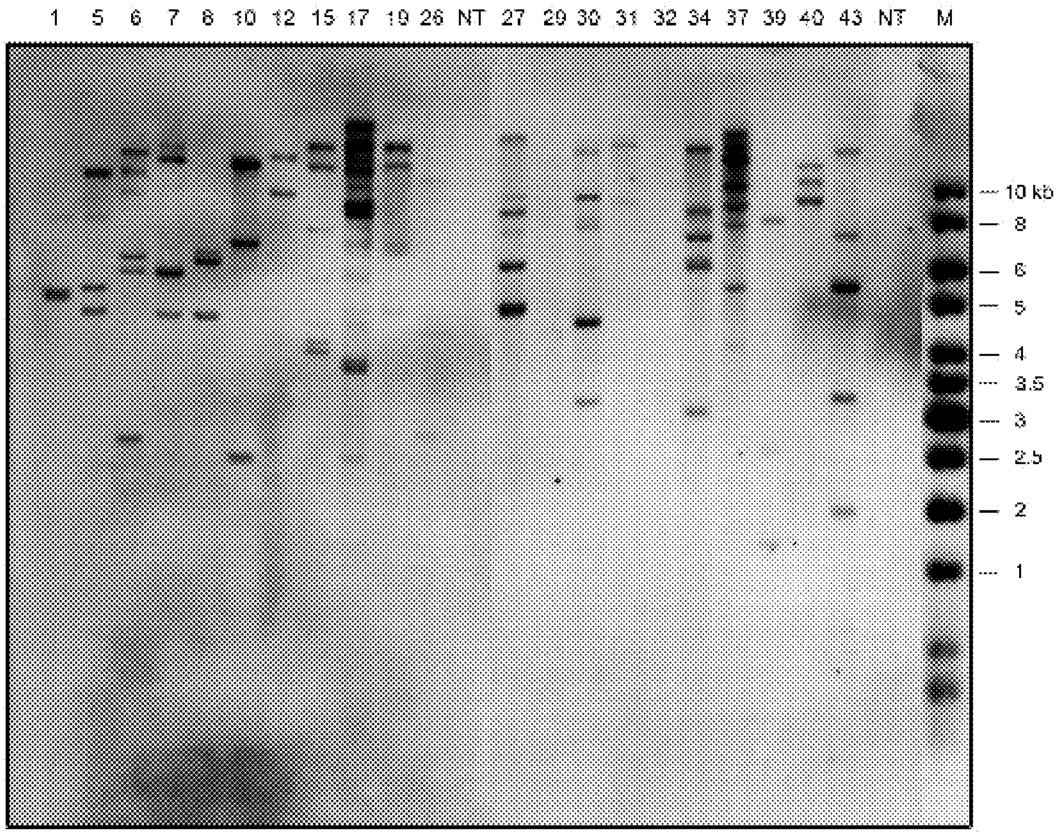
FIG. 3 is an image showing Southern hybridization analysis of transgenic banana lines according to one embodiment of the present invention. Lane numbers correspond to transgenic line names. (M): molecular weight markers. (NT): non-transformed lines. Transgenic lines with the constructs illustrated in FIG. 1B are: Construct M1, line 27; Construct AS1, lines 19, 26, 30, and 32; Construct PR1, lines 1, 5, 8, 10, and 15; Construct R/PR1, lines 6, 7, 12, 17, 29, 31, 37, 39, 40, and 43.
Figure 5:
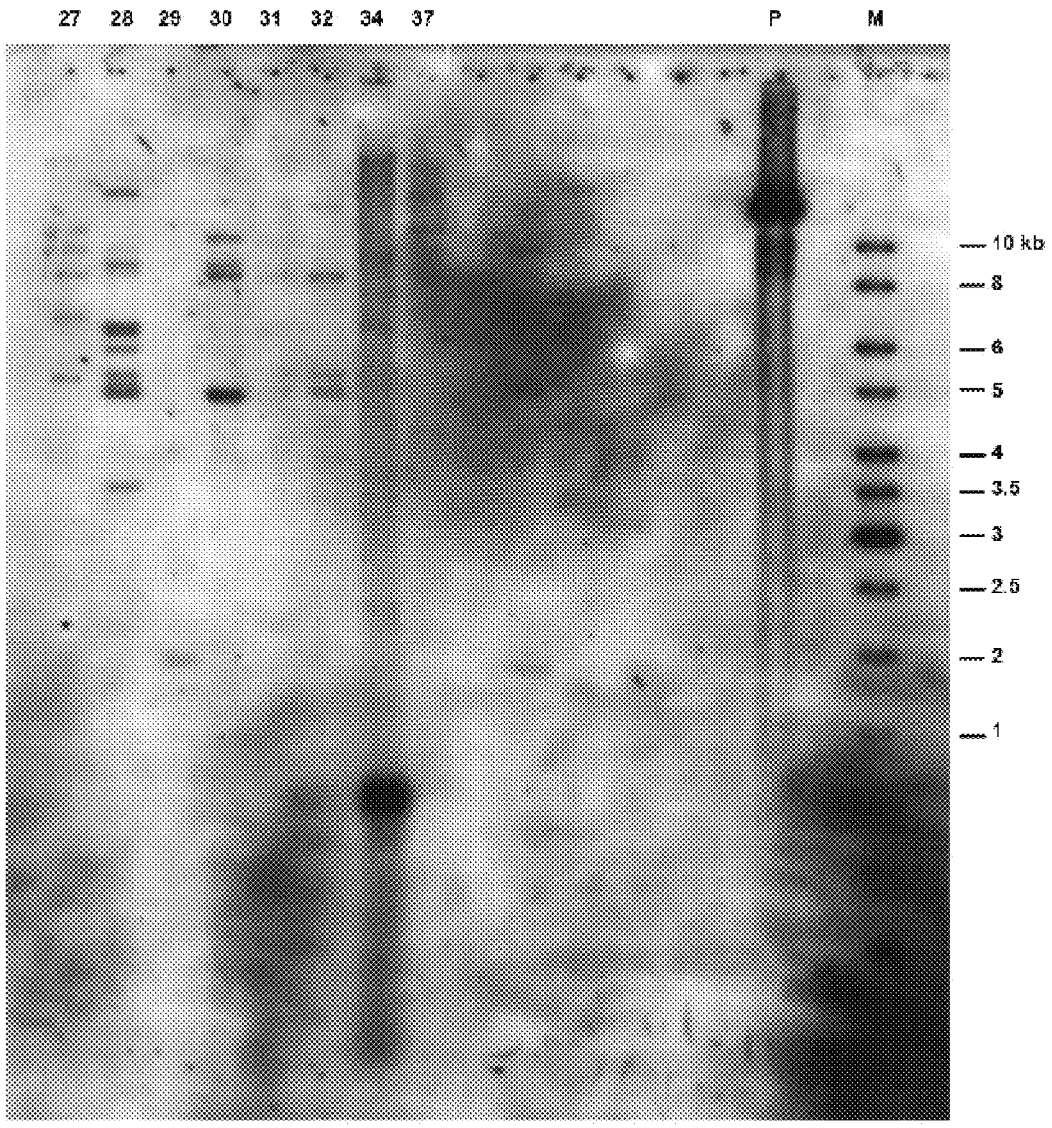
FIG. 5 is an image showing Southern hybridization analysis of transgenic banana lines according to one embodiment of the present invention. Lane numbers correspond to transgenic line names. (M): molecular weight markers. (P): plasmid control. Transgenic lines with the constructs illustrated in FIG. 1B are: Construct M1, line 27; Construct AS1, lines 28, 30, and 32; Construct R/PR1, lines 29, 31, and 37.

DNA isolated from the putatively transgenic BBTV-resistant banana plants hybridized to the probe prepared from the NPTII gene of vector pBI121. All of the resistant lines are independent transformants since each line displayed a unique hybridization pattern. Southern analyses confirmed that transgene integration had occurred in these lines (FIG. 3 and FIG. 5), and that between 3 and more than 10 copies of the transgene were present in these lines.

Example 10

BBTV Resistant Plant Line: Phenotypic Designation "M1"

Construct M1

Figure 8:
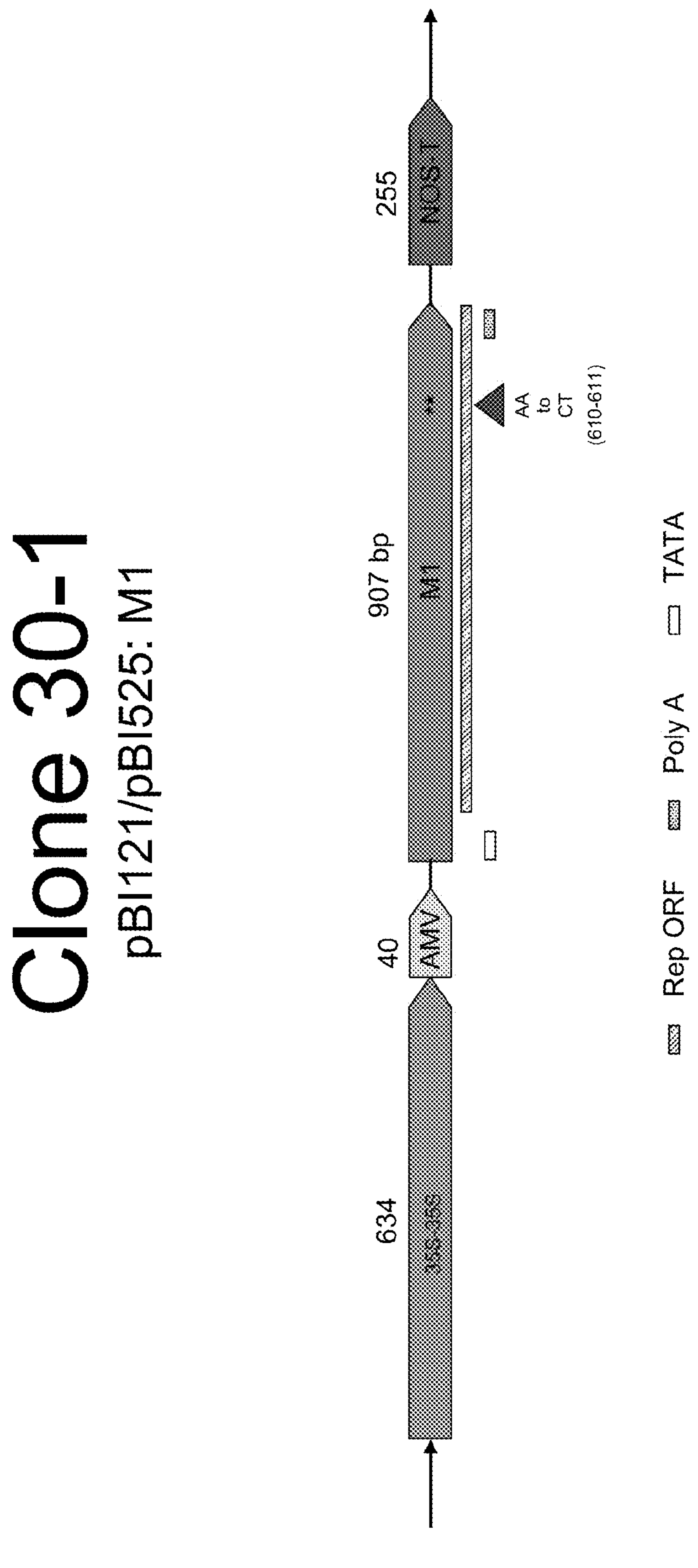
FIG. 8 is a schematic illustration of Clone 30-1, which includes Construct M1.

Mutant BBTV Rep gene in plasmid pBI121 (FIG. 8).

Mode of Transformation

*Agrobacterium tumefaciens*, disarmed.

Phenotype Description

Double point mutation of the replication associated protein (Rep) gene of the Hawaiian isolate of BBTV in sense orientation with respect to the double-35S CaMV promoter and AMV enhancer regions of the vector pBI525 subcloned into the transformation vector pBI121. The expression of this modified gene in transgenic banana plants is predicted to produce a non-functional Rep protein. Either the expression of this protein or the production of the aberrant RNA message encoding it is predicted to negatively regulate the production of functional BBTV Rep protein and replication of BBTV in plants challenged with BBTV.

Genotype

Gene Silencer.

Promoter: 35S from Cauliflower mosaic caulimovirus—constitutive eukaryotic gene promoter in plants. Enhancer: untranslated leader sequence from Alfalfa mosaic alfamovirus—cis-acting translation activator. Gene:

mutant replication associated protein from BBTV Hawaiian isolate—replication associated proteingene ORF from component 1 of the Hawaiian BBTV isolate, including the entire coding region of the replication associated protein (Rep) gene containing two single-point mutations and the poly-A tail motif. Also included are 52 bp of the 5'-UTR including the putative TATA box, and 36 bp of the 3'-UTR both from the Hawaiian BBTV isolate. All constructs are in sense orientation relative to the promoter, enhancer, and terminator in the vector. Terminator: Nopaline synthase from *Agrobacterium tumefaciens*—3' NOS from *Agrobacterium* T-DNA.

Selectable Marker.

Promoter: nos from *Agrobacterium tumefaciens*—nos promoter. Gene: nptII from *Klebsiella pneumoniae*—nptII gene from Tn5 from *Klebsiella pneumoniae*. Terminator: nos from *Agrobacterium tumefaciens*—nos terminator.

Example 11

BBTV Resistant Plant Line: Phenotypic Designation "AS1"

Construct AS1

Figure 7:
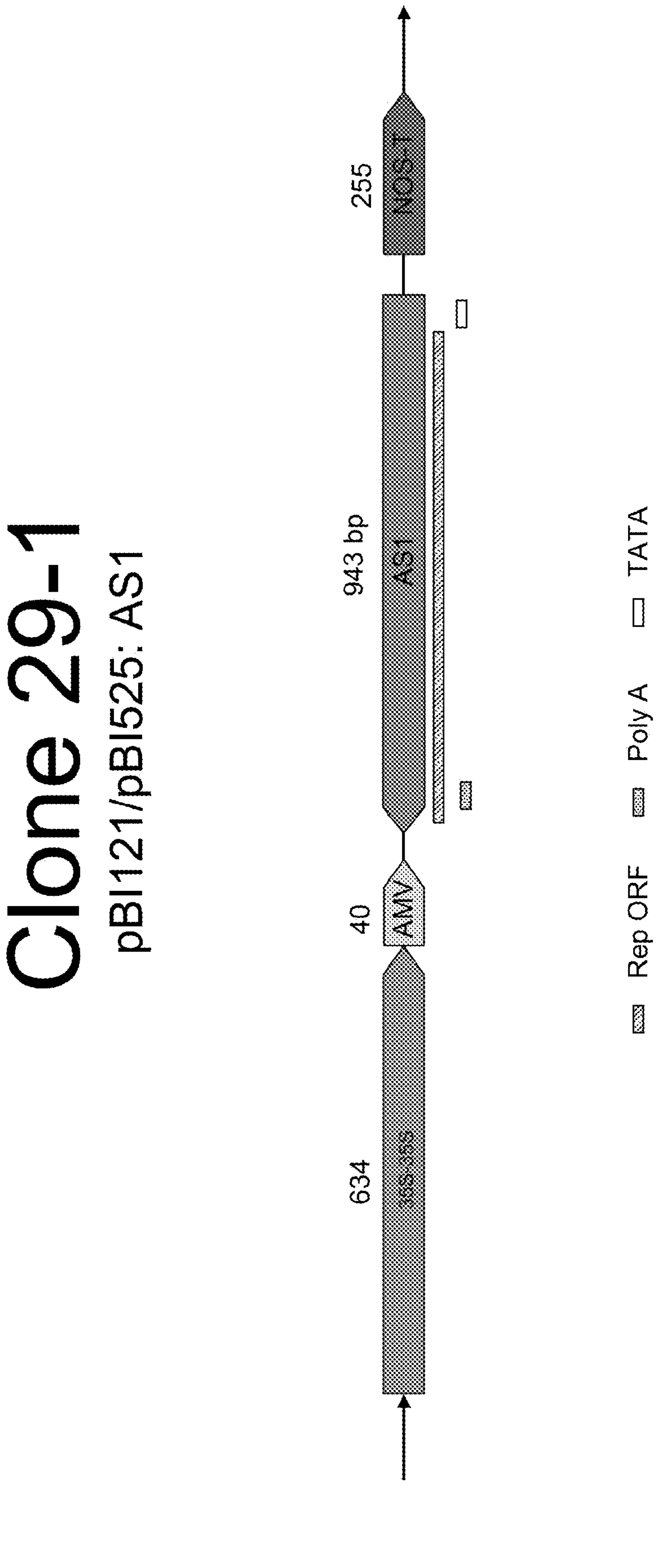
FIG. 7 is a schematic illustration of Clone 29-1, which includes Construct AS 1.

Antisense BBTV Rep gene in plasmid pBI121 (FIG. 7).

Mode of Transformation

*Agrobacterium tumefaciens*, disarmed.

Phenotype Description

The replication associated protein (Rep) gene of the Hawaiian isolate of BBTV in antisense orientation with respect to the double-35S CaMV promoter and AMV enhancer regions of the vector pBI525 subcloned into the transformation vector pBI121. Expression of this modified gene in transgenic banana plants is predicted to produce a non-functional Rep protein. The production of an aberrant RNA message encoding the antisense Rep gene is predicted to negatively regulate the production of functional BBTV Rep protein and replication of BBTV in plants challenged with BBTV.

Genotype

Gene Silencer.

Promoter: double $^{35}$S from Cauliflower mosaic caulimovirus—35S gene from Cauliflower mosaic caulimovirus. Enhancer: untranslated leader sequence from Alfalfa mosaic alfamovirus—cis-acting translational activator. Gene: replication associated protein (Rep) gene from BBTV, Hawaiian isolate—replication associated protein (Rep) gene ORF from component 1 of the Hawaiian BBTV isolate, including the entire coding region of the replication associated protein (Rep) gene and the poly-A tail motif. Also included are 52 bp of the 5'-UTR including the putative TATA box, and 36 bp of the 3'-UTR both from the Hawaiian BBTV isolate. All constructs are in antisense orientation relative to the promoter, enhancer, and terminator in the vector. Terminator: Nopaline synthase from *Agrobacterium tumefaciens*—3' NOS from *Agrobacterium* T-DNA region.

Selectable Marker. Promoter: nos from *Agrobacterium tumefaciens*—nos promoter. Gene: nptII from *Klebsiella pneumoniae*—nptII gene from Tn5 from *Klebsiella pneumoniae*. Terminator: nos from *Agrobacterium tumefaciens*—nos terminator.

Example 12

BBTV Resistant Plant Line: Phenotypic Designation "PR1"

Construct PR1

Figure 9:
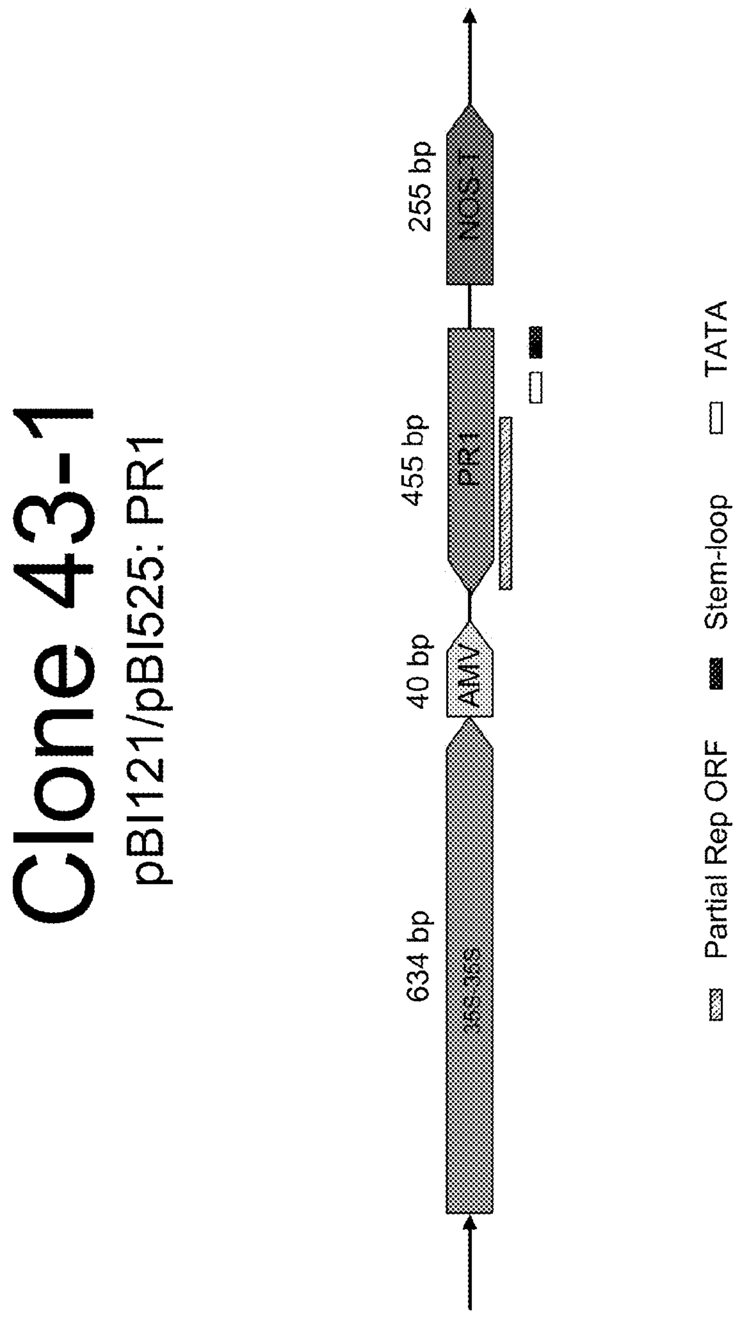
FIG. 9 is a schematic illustration of Clone 43-1, which includes Construct PR1.

Partial BBTV Rep gene in plasmid pBI121 (FIG. 9).

Mode of Transformation

*Agrobacterium tumefaciens*, disarmed.

Phenotype Description

Partial gene sequence of the replication associated protein (Rep) gene of the Hawaiian isolate of BBTV in antisense orientation with respect to the double-35S CaMV promoter and AMV enhancer regions of the vector pBI525 subcloned into the transformation vector pBI121. The expression of this truncated gene in transgenic banana plants will produce a non-functional Rep protein. The production of an aberrant RNA message from this partial Rep gene is predicted to negatively regulate the production of functional BBTV Rep protein and replication of BBTV in plants challenged with BBTV.

Genotype

Gene Silencer.

Promoter: double 35S from Cauliflower mosaic caulimovirus—constitutive promoter of eukaryotic genes in plants. Enhancer: untranslated leader sequence from Alfalfa mosaic alfamovirus—cis-acting translational activator. Gene: partial replication associated protein (Rep) gene from BBTV, Hawaiian isolate. The first 352 bp from the 5'-end of the replication associated protein (Rep) gene ORF from component 1 of the Hawaiian BBTV isolate. Also included is 104 bp of the 5'-UTR immediately upstream from the replication associated protein (Rep) gene ORF from component 1 of the Hawaiian BBTV isolate which contains the conserved stem-loop motif and the potential TATA box motif. All are in antisense orientation relative to the promoter, enhancer, and terminator in the vector. Terminator: Nopaline synthase from *Agrobacterium tumefaciens*—3' NOS from *Agrobacterium* T-DNA region.

Selectable Marker.

Promoter: nos from *Agrobacterium tumefaciens*—nos promoter. Gene: nptII from *Klebsiella pneumoniae*—nptII gene from Tn5 from *Klebsiella pneumoniae*. Terminator: nos from *Agrobacterium tumefaciens*—nos terminator.

Example 13

BBTV Resistant Plant Line: Phenotypic Designation Name R/PR1

Construct R/PR1

Figure 10:
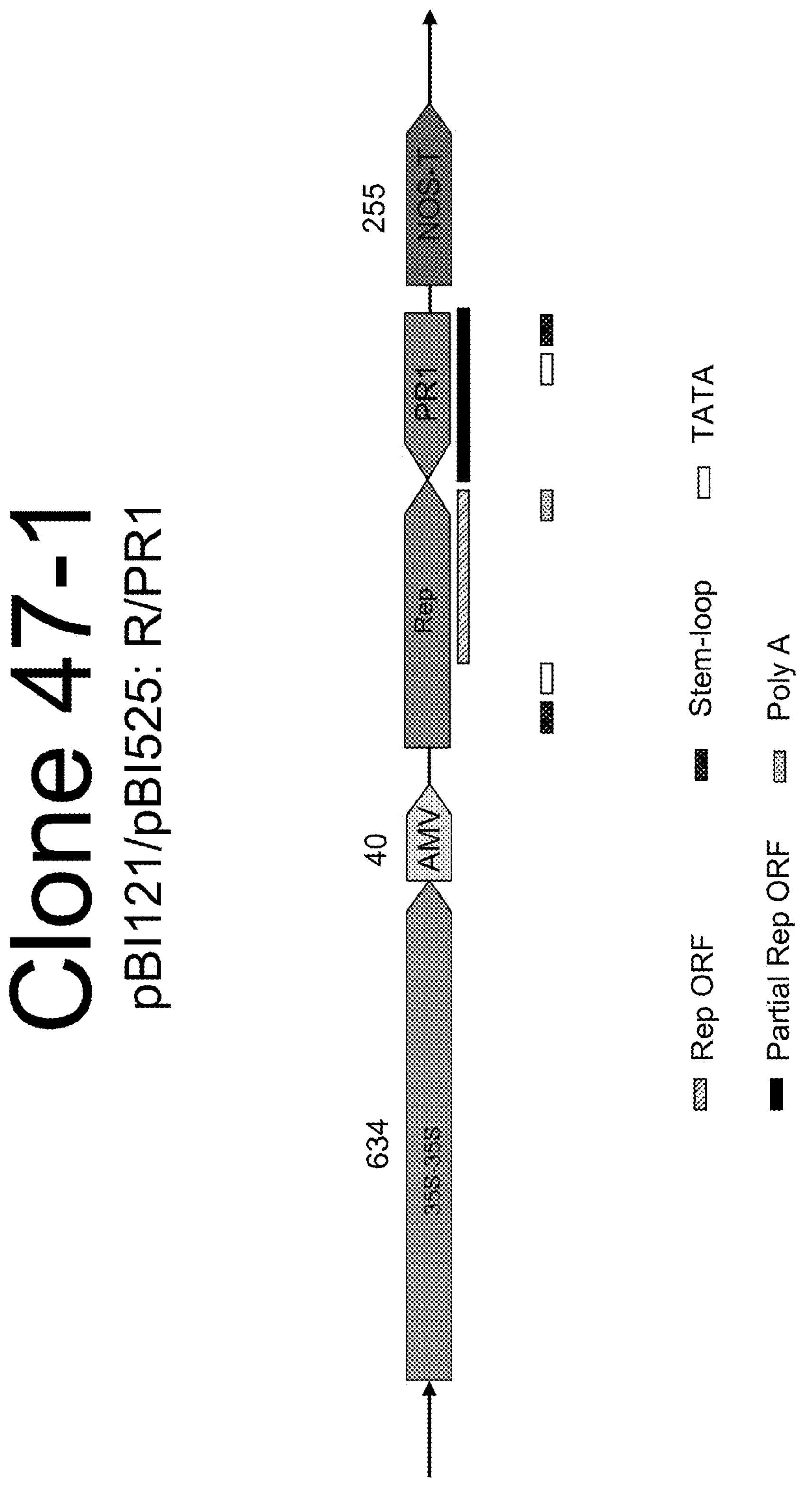
FIG. 10 is a schematic illustration of Clone 47-1, which includes Construct R/PR1.

Partial/full-length BBTV Rep gene fusion in plasmid pBI121 (FIG. 10).

Mode of Transformation

*Agrobacterium tumefaciens*, disarmed.

Phenotype Description

Partial gene sequence of the replication associated protein (Rep) gene of the Hawaiian isolate of BBTV in antisense orientation with respect to the double-35S CaMV promoter and AMV enhancer regions of the vector pBI525 subcloned into the transformation vector pBI121. This construct is fused to the full-length BBTV Rep gene in sense orientation. The expression of this construct in transgenic banana plants will produce a non-functional Rep protein. The production of the aberrant RNA message from this partial Rep gene is predicted to activate gene silencing mechanisms to negatively regulate the production of functional BBTV Rep protein and replication of BBTV in plants challenged with BBTV.

Genotype

Gene Silencer.

Promoter: double 35S from Cauliflower mosaic caulimovirus—constitutive promoter for transgenes in plants. Enhancer: untranslated leader sequence from Alfalfa mosaic alfamovirus—cis-acting transcriptional activator. Gene: replication-partial replication inverted repeat from BBTV, Hawaiian isolate. The replication associated protein (Rep) gene ORF from component 1 of the Hawaiian BBTV isolate that includes the entire coding region of the replication associated protein (Rep) gene and the poly-A tail motif. Also included are 104 hp of the 5'-UTR including the putative TATA box, and 126 bp of the 3'-UTR which contains the conserved stem-loop motif and the potential TATA box motif, both from component 1 of the Hawaiian BBTV isolate. This construct is in sense orientation relative to the promoter, enhancer, and terminator in the vector. Fused to the 3'-end of this entire construct, in antisense orientation, is the first 352 bp from the 5'-end of the replication associated protein (Rep) gene ORF from component 1 of the Hawaiian isolate of BBTV and 104 bp of the 5'-UTR immediately upstream from the replication associated protein (Rep) gene ORF which contains the conserved stem loop motif and the potential TATA box motif from component 1 of the Hawaiian isolate. The resulting construct is composed of the entire ORF of the replication associated protein (Rep) gene ORF including the 5'-UTR and 3'-UTR in sense orientation, fused to the first 352 bp from the 5'-end of the replication associated protein (Rep) gene ORF and including 104 bp of the 5'-UTR immediately upstream from the replication associated protein (Rep) gene ORF that contains the conserved stem-loop motif and the potential TATA box motif Terminator: Nopaline synthase from *Agrobacterium tumefaciens*—3' NOS from *Agrobacterium* T-DNA region.

Selectable Marker.

Promoter: nos from *Agrobacterium tumefaciens*—nos promoter. Gene: nptII from *Klebsiella pneumoniae*—nptII gene from Tn5 from *Klebsiella pneumoniae*. Terminator: nos from *Agrobacterium tumefaciens*—nos terminator.

Advances in molecular biology and biotechnology have led to the successful development and commercial release in the United States of several virus resistant crops including papaya resistant to Papaya ringspot virus (Gonsalves, "Control of Papaya Ringspot Virus in Papaya: A Case Study," *Annual Review of Phytopathology* 36(1):415-437 (1998), which is hereby incorporated by reference in its entirety), potato resistant to Potato virus Y (Smith et al., "Transgenic Potato Virus Y Resistance in Potato: Evidence for an RNA-mediated Cellular Response,"*Phytopathology* 85(8):864-870 (1995), which is hereby incorporated by reference in its entirety) and Potato leafroll virus (Duncan et al., "Field Performance of Transgenic Potato, with Resistance to Colorado Potato Beetle and Viruses," *HortScience* 37(2):275-276 (2002), which is hereby incorporated by reference in its entirety), and a squash cultivar resistant to three viruses: Cucumber mosaic virus, Watermelon mosaic virus-2, and Zucchini yellow mosaic virus (Fuchs et al., "Comparative Virus Resistance and Fruit Yield of Transgenic Squash with Single and Multiple Coat Protein Genes," *Plant Disease* 82(12):1350-1356 (1998), which is hereby incorporated by reference in its entirety). All of these viruses have RNA genomes, and all plants are resistant due to RNA silencing (also referred to as posttranscriptional gene silencing) of the transgene. RNA silencing was first reported in plants (Napoli et al., "Introduction of a Chimeric Chalcone Synthase Gene Into Petunia Results in Reversible Co-suppression of Homologous Genes in Trans," *Plant Cell* 2(4):279-289 (1990), which is hereby incorporated by reference in its entirety), and has been shown to result from the degradation of RNAs with sequence homology to the inducer which may be a virus, transgene, transposable element, or dsRNA (Hamilton et al., "A Species of Small Antisense RNA in Posttranscriptional Gene Silencing in Plants," *Science* 286 (5441):950-952 (1999), which is hereby incorporated by reference in its entirety). Transgenic papaya resistant to the Papaya ringspot virus has allowed the Hawaii papaya industry to recover from the severe damage caused by the virus (Gonsalves et al., "Control of Papaya Ringspot Virus in Papaya: A Case Study," *Annual Review of Phytopathology* 36(1):415-437 (1998), which is hereby incorporated by reference in its entirety).

For viruses with DNA genomes, there are no reports of immunity to virus infection using the RNA silencing approach. Pooggin et al., "RNAi Targeting of DNA Virus in Plants," *Nature Biotechnology* 21:131-132 (2003), which is hereby incorporated by reference in its entirety, reported recovery of *Vigna mungo* (blackgram) from *Vigna mungo* yellow mosaic virus, a bipartite geminivirus, after bombarding infected seedlings with a construct designed to express a double-stranded RNA that was homologous to the virus promoter sequence. This recovery was believed to be due to transcriptional silencing of the virus promoter and not RNA silencing. Seemanpillai et al., "Transcriptional Silencing of Geminiviral Promoter-Driven Transgenes Following Homologous Virus Infection," *Molecular Plant-Microbe Interactions* 16(5):429-438 (2003), which is hereby incorporated by reference in its entirety, also reported transcriptional silencing of a geminivirus promoter, which was associated with cytosine hypermethylation. Vanitharani et al., "Short Interfering RNA-mediated Interference of Gene Expression and Viral DNA Accumulation in Cultured Plant Cells," *PNAS* 100(16):9632-9636 (2003), which is hereby incorporated by reference in its entirety, reported reduced accumulation of AC1 mRNA and genomic DNA of African cassava mosaic virus, also a bipartite geminivirus, using small interfering RNAs targeted against AC1 in *N. tabacum* protoplasts.

A second strategy to generate resistance to viruses with DNA genomes is by expressing a mutated or truncated Rep protein. Lucioli et al., "Tomato Yellow Leaf Curl Sardinia Virus Rep-Derived Resistance to Homologous and Heterologous Geminiviruses Occurs by Different Mechanisms and Is Overcome if Virus-Mediated Transgene Silencing Is Activated," *Journal of Virology* 77(12):6785-6798 (2003), which is hereby incorporated by reference in its entirety, reported resistance to homologous and heterologous geminiviruses in plants expressing the N-terminal 210 amino acids of the Rep gene from Tomato yellow leaf curl Sardinia virus ("TYLCSV"). Resistance to homologous virus was due to inhibition of viral transcription and replication while resistance to the heterologous virus, Tomato yellow leaf curl virus ("TYLCV"), was due to interaction between the oligomerization domains of the TYLCSV Rep transgene and the TYLCV Rep.

In the present invention, twenty-one independently-transformed 'Dwarf Brazilian' banana plants were produced using the four different constructs of the BBTV replication associated protein (Rep) gene described in Examples 10-13 herein. These plant lines have been shown to be resistant to infection by BBTV. None of these plants developed any bunchy top symptoms following challenge by viuliferous aphids, and no replication of BBTV could be detected in these plants using PCR designed to detect the coat protein gene of BBTV. These resistant plants have been shown to contain genes from the transformation vector, and these transgenes are not present in susceptible wild-type plants. The genetically engineered plants that have been produced represent the only banana of any variety that have demonstrable BBTV resistance. Since banana plants are exclusively vegetatively propagated, these resistant plants can be used to produce many individuals with the same resistance characteristics. Farmers who grow these resistant plants will be able to replant their fields in the usual way by transplanting young suckers that arise from recently-harvested resistant plants. These suckers will also have BBTV-resistance. The approach that has been developed to produce these plants will be applicable to other banana varieties, with other useful horticultural characteristics. The BBTV-resistant banana plants will be vegetatively propagated through tissue culture to produce a large number of identical plants that will be rechallenged with BBTV and also evaluated for field resistance to BBTV. Other horticultural characteristics of these plants will also be evaluated in the field.

Prohetic Example 14

Field Trial

Field Plot Design

The objective of this field trial is to test the level of resistance to BBTV of plants that have been engineered to contain sequences of the replication associated protein (Rep) gene of a Hawaiian BBTV isolate. Virus inoculation of all test plants will be achieved through viruliferous aphids, either spreading naturally from adjacent banana plantings affected with bunchy top disease or by placing aphids collected from BBTV infected source plants directly onto test plants. Movement and spread of insects within the test plot will be monitored to assure exposure of all test plants to BBTV inoculum.

Field Site Location

The University of Hawaii Agricultural Research Station in the community of Waimanalo, Oahu is the location of the proposed field trial. The farm consists of about 130 acres currently planted in papaya, banana, guava, ornamentals, corn, turf grass, sweet potato, tomato, soybean, mango, macadamia nut, and tropical trees. The experiment station has several full-time staff including the manager who lives on the station. There is a single entrance that is gated and locked at night and on weekends, and a 6 ft. tall chain-link fence surrounds the entire station. The station is bordered on one side by a USDA-APHIS fruit fly facility and on the other sides by residential and agricultural areas.

Field Design

Transgenic banana will be planted together with non-transgenic banana of the same cultivar, which will serve as positive controls for infection. Plants will be spaced approximately 2 meters (m) apart within double rows, 4 m between double rows, and will be arranged in a randomized complete block design with 2-3 replicates, depending on the number of plants produced per line and the number of lines. Fertilizer and pesticide applications and cultural practices (weeding, thinning, etc.) will mirror Hawaii growers' practices, except insecticide will not be applied to control aphids.

BBTV is now found in other fields on the experiment station and in areas surrounding the farm. It is expected that all control plants will quickly become infected, but if this does not occur 20 aphids raised on BBTV infected banana will be placed onto plants. This procedure will be repeated each month until all non-transgenic plants have become infected with BBTV. BBTV infection will be monitored based on visual observations and will be confirmed with serological and molecular techniques. Transgenic plants that become systemically infected with BBTV will be removed from the field, and the mat will be destroyed by injection of herbicide.

Data Collection

BBTV infection will be monitored based on visual observations and will be confirmed with serological and molecular techniques. Data will be taken on horticultural characteristics including height at flowering, time from transplanting to flowering, time from flowering to harvest, fruit yield, size, shape and appearance, sucker production, and growth rate. ANOVA will be used to analyze yield data, and repeated measures ANOVA will be used to analyze growth data.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A transgenic plant, component thereof or fruit thereof, of the genus *Musa*, comprising a nucleic acid construct comprising a) a nucleic acid molecule selected from the group consisting of i) a first segment which is a sense form of Banana Bunchy Top Virus (BBTV) replication associated protein (Rep) gene and a second segment which is an antisense form of a partial BBTV replication associated protein (Rep) gene, wherein the first and second segments are linked to one another; and ii) a sense form of BBTV replication associated protein (Rep) gene having a mutation corresponding to a mutation of Adenine to Cytosine at base 687 of SEQ ID NO: 1, and a mutation of Adenine to Thymine at position 688 of SEQ ID NO: 1 (AA→CT);

b) a 5' DNA promoter sequence; and c) a 3' terminator sequence;

wherein the nucleic acid molecule, the promoter, and the terminator are operatively coupled to permit transcription of the nucleic acid molecule, and the nucleic acid molecule is positioned in the nucleic acid construct to result in suppression or interference of BBTV, wherein the plant is resistant to Banana bunchy top virus.

2. The transgenic plant, component thereof or fruit thereof, of claim 1, wherein the nucleic acid molecule i) further comprises a stem loop structure proximate to an end of the first segment.

3. The transgenic plant, component thereof or fruit thereof, of claim 2, wherein the stem loop structure has the sequence of SEQ ID NO:18.

4. The transgenic plant, component thereof or fruit thereof, of claim 1, wherein the nucleic acid molecule i) further comprises a stem loop structure proximate to an end of the second segment.

5. The transgenic plant, component thereof or fruit thereof, of claim 4, wherein the stem loop structure has the sequence of SEQ ID NO:18.

6. The transgenic plant, component thereof or fruit thereof, of claim 4, wherein the first segment is positioned in the construct so as to be transcribed before the second segment.

7. The transgenic plant, component thereof or fruit thereof, of claim 1, wherein the DNA promoter is a constitutive promoter.

8. The transgenic plant, component thereof or fruit thereof, of claim 1, wherein the DNA promoter is an inducible plant promoter.

9. The transgenic plant, component or fruit according to claim 1, wherein the plant is a banana or a plantain plant.

10. A method of imparting BBTV resistance to a plant of the genus *Musa*, said method comprising:

a) transforming a plant or plant cell of the genus *Musa* with a nucleic acid construct comprising i) a nucleic acid molecule selected from the group consisting of A) a first segment which is a sense form of Banana Bunchy Top Virus (BBTV) replication associated protein (Rep) gene and a second segment which is an antisense form of a partial BBTV replication associated protein (Rep) gene, wherein the first and second segments are linked to one another; and B) a sense form of BBTV replication associated protein (Rep) gene having a mutation corresponding to a mutation of Adenine to Cytosine at base 687 of SEQ ID NO: 1, and a mutation of Adenine to Thymine at position 688 of SEQ ID NO: 1 (AA→CT);

ii) a 5' DNA promoter sequence; and iii) a 3' terminator sequence;

wherein the nucleic acid molecule, the promoter, and the terminator are operatively coupled to permit transcription of the nucleic acid molecule, and the nucleic acid molecule is positioned in the nucleic acid construct to result in suppression or interference of BBTV; and b) growing the transformed plant or plant cell under conditions effective to impart BBTV resistance to the plant.

11. The method according to claim 10, wherein said transforming is *Agrobacterium* mediated.

12. The method according to claim 10, wherein said transforming comprises:

propelling particles coated with an expression vector comprising the nucleic acid construct at plant cells under conditions effective for the particles to penetrate into the cell interior, thus introducing the expression vector into the cell interior.

13. A plant cell of the genus *Musa* comprising a nucleic acid construct 4-comprising:

a) a nucleic acid molecule selected from the group consisting of i) a first segment which is a sense form of Banana Bunchy Top Virus (BBTV) replication associated protein (Rep) gene and a second segment which is an antisense form of a partial BBTV replication associated protein (Rep) gene, wherein the first and second segments are linked to one another; and ii) a sense form of BBTV replication associated protein (Rep) gene having a mutation corresponding to a mutation of Adenine to Cytosine at base 687 of SEQ ID NO: 1, and a mutation of Adenine to Thymine at position 688 of SEQ ID NO: 1 (AA→CT);

b) a 5' DNA promoter sequence; and c) a 3' terminator sequence;

wherein the nucleic acid molecule, the promoter, and the terminator are operatively coupled to permit transcription of the nucleic acid molecule, and the nucleic acid molecule is positioned in the nucleic acid construct to result in suppression or interference of BBTV, and the nucleic acid construct is stably inserted into the genome, wherein the plant cell is capable of regenerating into a plant that is resistant to Banana bunchy top virus.

14. The plant cell of claim 13, that is a banana plant cell or a plantain plant cell.

* * * * *

UNITED STATES PATENT AND TRADEMARK OFFICE

CERTIFICATE OF CORRECTION

PATENT NO. : 8,901,372 B2
APPLICATION NO. : 12/712893
DATED : December 2, 2014
INVENTOR(S) : John Hu et al.

It is certified that error appears in the above-identified patent and that said Letters Patent is hereby corrected as shown below:

In the Claims

Column 73, Claim 13, line 22 reads "acid construct 4-comprising:" and should be corrected to read "acid construct comprising:"

Signed and Sealed this
Twenty-second Day of September, 2015

Michelle K. Lee
*Director of the United States Patent and Trademark Office*